US007678089B2

(12) United States Patent
Py et al.

(10) Patent No.: US 7,678,089 B2
(45) Date of Patent: Mar. 16, 2010

(54) DELIVERY DEVICE AND METHOD OF DELIVERY

(75) Inventors: Daniel Py, Stamford, CT (US); Julian V. Chan, Spring Valley, NY (US); Jeffrey M. Atwood, Orange, CT (US)

(73) Assignee: Medical Instill Technologies, Inc., New Milford, CT (US)

( * ) Notice: Subject to any disclaimer, the term of this patent is extended or adjusted under 35 U.S.C. 154(b) by 1348 days.

(21) Appl. No.: 10/990,164

(22) Filed: Nov. 15, 2004

(65) Prior Publication Data

US 2005/0165368 A1      Jul. 28, 2005

Related U.S. Application Data

(60) Provisional application No. 60/519,961, filed on Nov. 14, 2003.

(51) Int. Cl.
*A61H 33/04* (2006.01)
*A61M 35/00* (2006.01)
*B67D 5/42* (2006.01)
*G01F 11/00* (2006.01)

(52) U.S. Cl. .................. 604/302; 222/388; 604/294

(58) Field of Classification Search ............... 604/295, 604/294, 289, 19, 68, 9, 30, 34, 22, 35, 27, 604/32, 521, 119, 65, 67, 153, 167.01, 541; 137/484.2, 15.19, 595, 614.19, 487.5, 541; 222/212, 105, 129; 251/129.12, 129.21, 251/174
See application file for complete search history.

(56) References Cited

U.S. PATENT DOCUMENTS

| 4,650,461 A | | 3/1987 | Woods |
| 4,896,794 A | * | 1/1990 | Banks et al. .................... 222/1 |
| 5,133,702 A | * | 7/1992 | Py .............................. 604/302 |

(Continued)

OTHER PUBLICATIONS

"The New Standard in Eyedrop and Contact lens delivery." OMedInstill. (c) 2003.*

(Continued)

*Primary Examiner*—Nicholas D Lucchesi
*Assistant Examiner*—Ian K Holloway
(74) *Attorney, Agent, or Firm*—McCarter & English, LLP

(57) ABSTRACT

An ophthalmic delivery device includes a body defining a fluid reservoir and a pump in fluid communication with the reservoir. The delivery device also includes a nozzle that includes a dosage chamber for holding a dosage of fluid, a valve seat, and a valve cover. The valve cover extends about the valve seat and forms an interface therebetween and the valve seat includes an outlet aperture. The interface is in fluid communication with the outlet aperture and the dosage chamber, and at least part of the valve cover is movable between (i) a closed position with the valve cover engaging the valve seat to close the interface and form a fluid-tight seal therebetween, and (ii) an open position with at least part of the valve cover spaced away from the valve seat in response to fluid flowing through the outlet aperture at a pressure greater than a valve opening pressure to allow the passage of pressurized fluid therebetween. The valve seat and the valve cover are dimensioned to dispense the dosage of fluid through the interface at a velocity of equal to or less than 6 meters per second.

40 Claims, 20 Drawing Sheets

U.S. PATENT DOCUMENTS

| | | |
|---|---|---|
| 5,207,659 A | 5/1993 | Pennaneac'h et al. |
| 5,360,145 A | 11/1994 | Gueret |
| 5,411,176 A | 5/1995 | Favre |
| 5,630,793 A | 5/1997 | Rowe |
| 5,836,484 A | 11/1998 | Gerber |
| 5,855,322 A | 1/1999 | Py |
| 5,875,931 A | 3/1999 | Py |
| 5,881,956 A | 3/1999 | Cohen et al. |
| 6,053,433 A | 4/2000 | Py |
| 6,450,994 B1 * | 9/2002 | Boyles et al. ............... 604/294 |
| 6,506,183 B2 | 1/2003 | Cogger |
| 6,524,287 B1 | 2/2003 | Cogger |
| RE38,077 E | 4/2003 | Cohen et al. |
| 6,662,977 B2 | 12/2003 | Gerber et al. |
| D492,192 S * | 6/2004 | Py et al. ...................... D9/688 |
| 6,997,219 B2 * | 2/2006 | Py et al. ...................... 141/314 |
| 2001/0044603 A1 * | 11/2001 | Harrold ...................... 604/152 |
| 2002/0074362 A1 * | 6/2002 | Py et al. ...................... 222/388 |
| 2002/0107493 A1 | 8/2002 | Cogger |
| 2002/0111580 A1 | 8/2002 | Richeal et al. |
| 2002/0130139 A1 | 9/2002 | Shiraishi et al. |
| 2003/0209567 A1 | 11/2003 | Crosnier et al. |

OTHER PUBLICATIONS

International Search Report for International Application No. PCT/US04/38345.

* cited by examiner

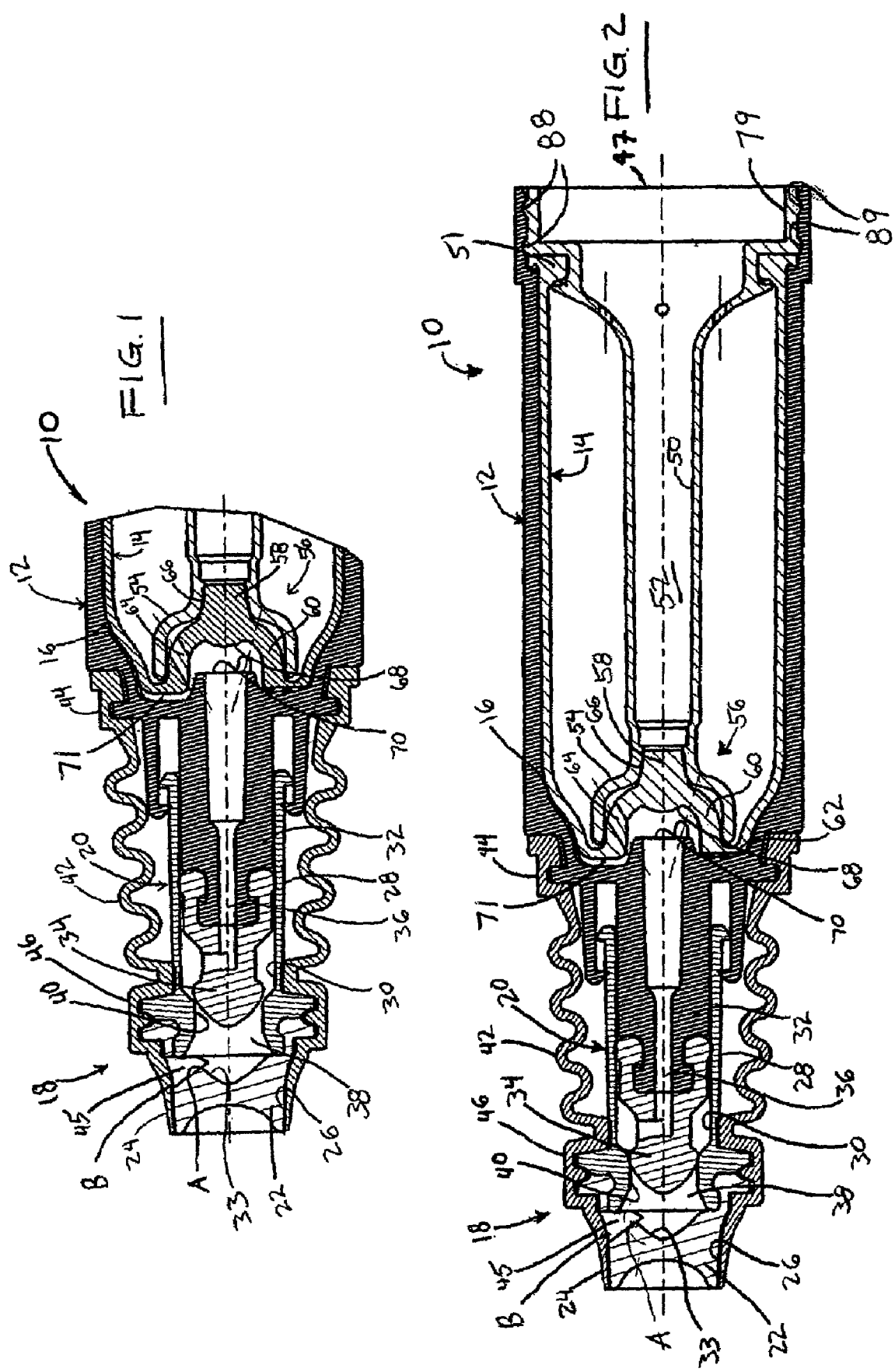

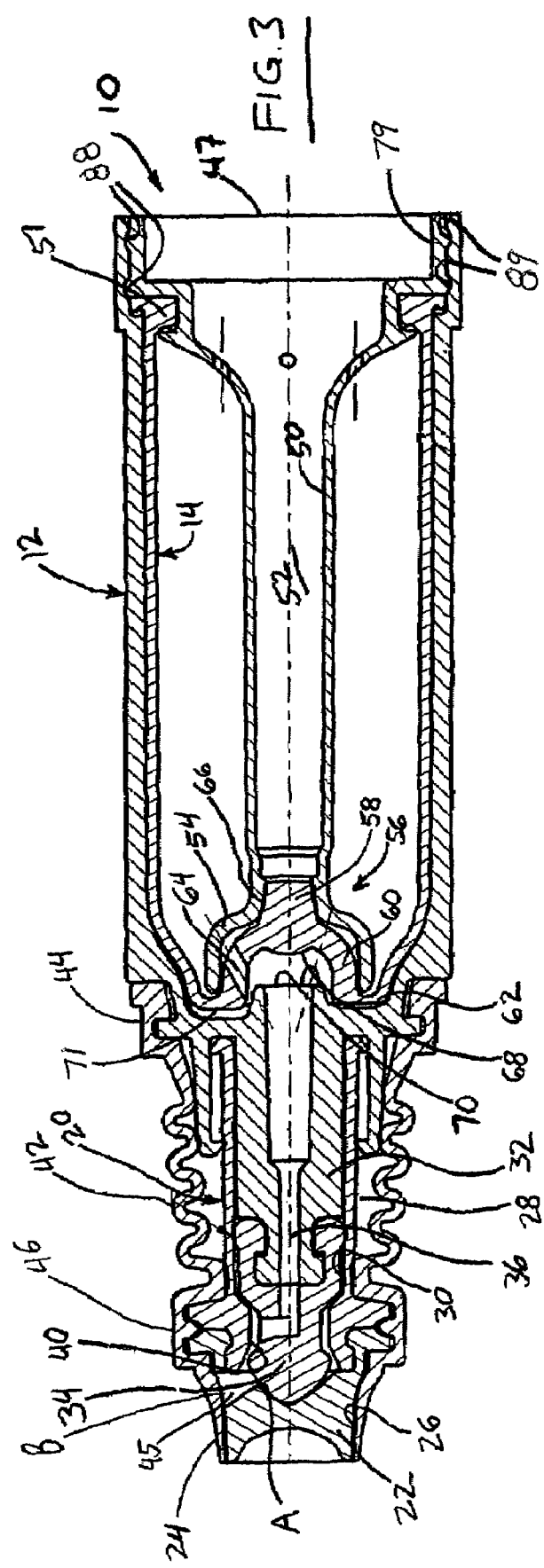

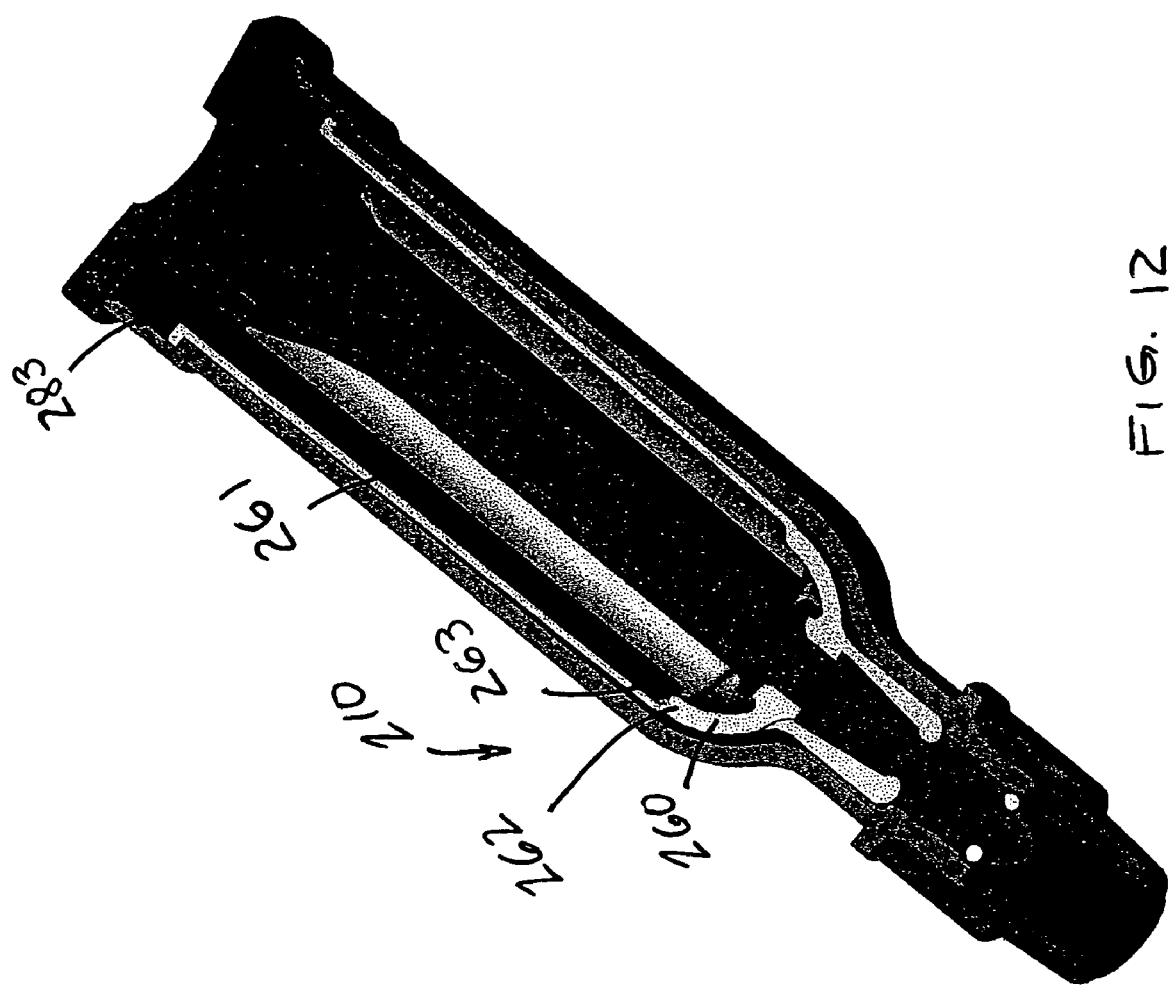

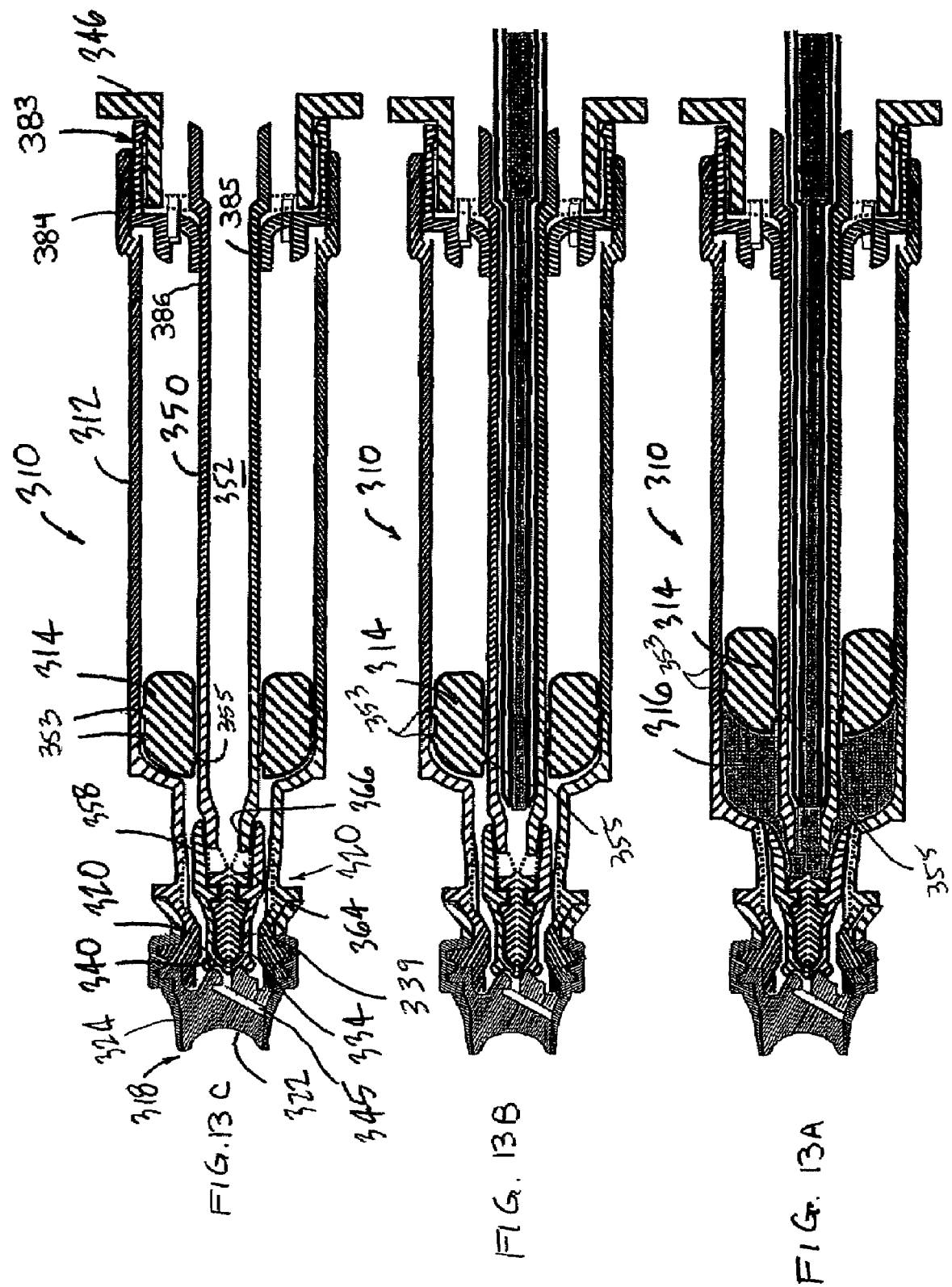

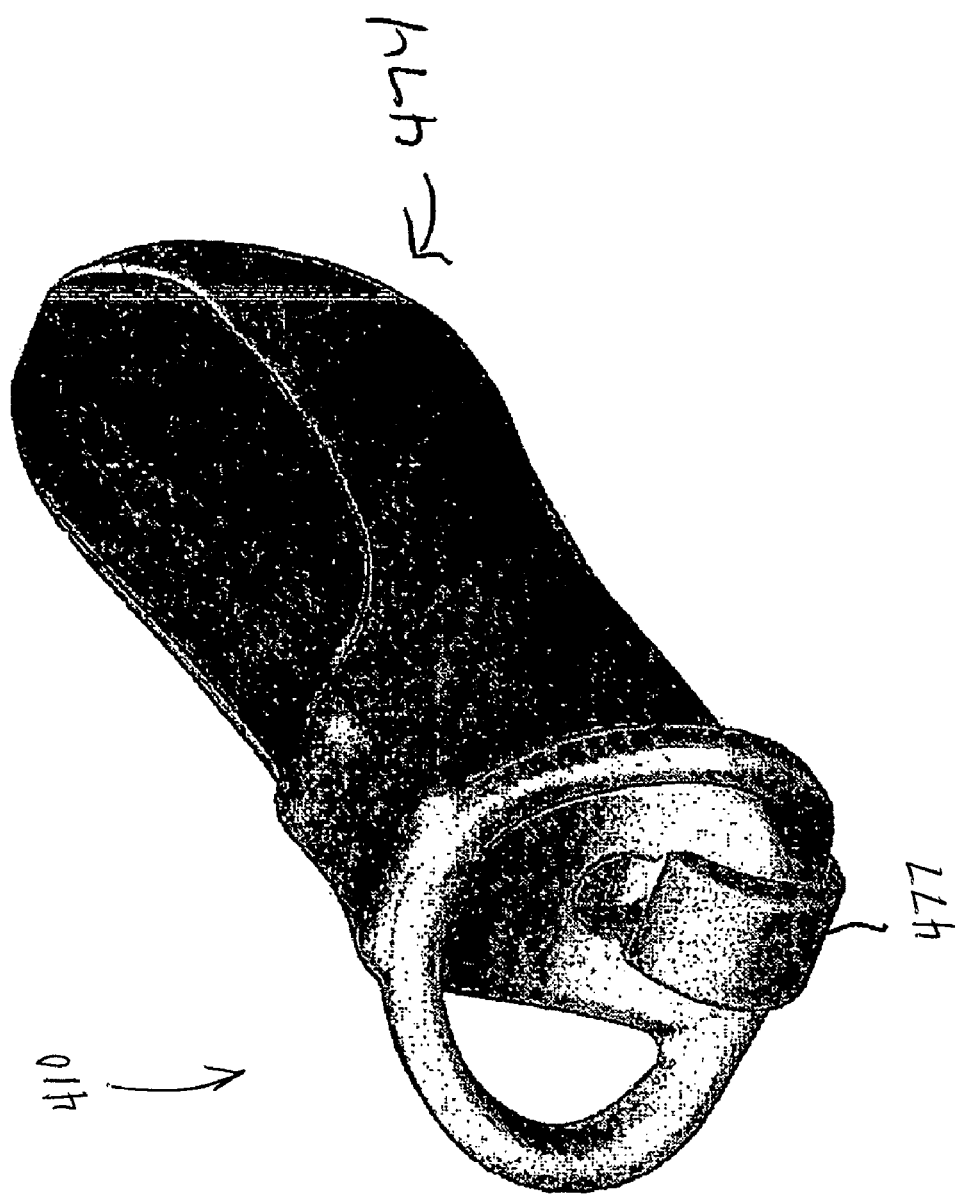

DELIVERY DEVICE AND METHOD OF DELIVERY

CROSS-REFERENCE TO RELATED APPLICATION

This patent application claims the benefit of U.S. Provisional Patent Application Ser. No. 60/519,961, filed Nov. 14, 2003, which is hereby expressly incorporated by reference as part of the present disclosure.

FIELD OF THE INVENTION

The present invention relates to delivery devices and methods of delivering fluids or other substances.

BACKGROUND INFORMATION

A typical prior art ophthalmic delivery device, such as an eye dropper, includes a vial for holding the fluid to be dispensed into the eye, and a cap and eye-dropper assembly. The cap includes a squeeze bulb for drawing fluid from the vial into a hollow tube of the dropper. The user must then hold the dropper over the eye, and squeeze the bulb to release a drop of fluid into an eye. One drawback associated with such prior art ophthalmic delivery devices is that many users have found them difficult to use. Some users have difficulty delivering drops into the eyes and instead spill the drops onto other parts of the face. Other users have difficulty measuring the dosage and/or manipulating the dropper. Another drawback is that it can be difficult to maintain sufficiently precise control over the volume of each drop from one drop to the next. Yet another drawback is that such prior art devices typically cannot hold multiple doses of non-preserved medicaments.

The present inventor has recognized these and other problems associated with prior art ophthalmic delivery devices and has provided improved ophthalmic delivery devices that overcome many of the problems encountered in the prior art. For example, the present inventor has provided an ophthalmic delivery device including a body defining therein a variable volume chamber for holding a reservoir of medicament; a piston-type pump coupled in fluid communication with the variable-volume chamber for pumping metered doses of medicament therefrom; a nozzle including a one-way valve coupled in fluid communication with the pump for dispensing from the device the pumped metered dosages of medicament; an actuator for actuating the pump by, for example, depressing the actuator with a finger; and an eyelid depressor for exposing the ocular cul-de-sac upon actuating the pump and automatically delivering a precise volume of medicament to the conjunctiva cul-de-sac. One of the issues encountered with such improved ophthalmic delivery devices is that the speed of the metered dosage delivered by the pump can be greater than the speed of a drop delivered by a traditional eye dropper, i.e., one that uses gravitational force to deliver a drop from the dropper tip toward the eye. Accordingly, the energy imparted to the eye upon impact of the dosages delivered by such mechanically actuated ophthalmic delivery devices can be greater than that of traditional gravity dispensed drops.

Accordingly, it is an object of the present invention to overcome one or more of the above-described drawbacks and/or disadvantages, and to provide an improved ophthalmic delivery device and method capable of delivering metered dosages of fluids onto an eye such that the energy imparted to the eye upon impact of the dosage is less than the energy imparted by previous mechanically-actuated ophthalmic delivery devices.

SUMMARY OF THE INVENTION

Exemplary embodiments of the invention include an ophthalmic delivery device including a body defining a fluid reservoir and a pump in fluid communication with the reservoir. The delivery device also includes a nozzle that includes a dosage chamber for holding a dosage of fluid, a valve seat, and a valve cover. The valve cover extends about the valve seat and forms an interface therebetween and the valve seat includes an outlet aperture. The interface is in fluid communication with the outlet aperture and the dosage chamber, and at least part of the valve cover is movable between (i) a closed position with the valve cover engaging the valve seat to close the interface and form a fluid-tight seal therebetween, and (ii) an open position with at least part of the valve cover spaced away from the valve seat in response to fluid flowing through the outlet aperture at a pressure greater than a valve opening pressure to allow the passage of pressurized fluid therebetween. The valve seat and the valve cover are dimensioned to dispense the dosage of fluid through the interface at a velocity of equal to or less than about 6 meters per second.

Additional exemplary embodiments include an ophthalmic delivery device that includes a first means for defining a variable-volume chamber for storing a substance to be delivered and a second means for pumping a metered dose of substance from the variable-volume chamber. There is also a third means in fluid communication with the second means for (i) forming a closed position defining a fluid-tight seal for preventing the passage of substance therethrough, and (ii) at least one open position for allowing a metered dose of substance pumped by the second means to flow therethrough and a fourth means for delivering the pumped dosage at a velocity exiting the third means of less than approximately 10 meters per second.

Exemplary embodiments of the invention further include a method for delivering a substance to an eye. The method includes storing multiple doses of the substance in a variable-volume chamber, pumping a metered dose of substance from the variable-volume chamber through a one-way valve defining a closed position forming a fluid-tight seal for preventing the passage of substance therethrough and at least one open position for allowing a metered dose of substance pumped by the second means to flow therethrough, and controlling the velocity of the pumped dose exiting the one-way valve to be less than approximately 10 meters per second.

Other exemplary embodiments include an ophthalmic dispenser comprising a body defining a fluid reservoir; and a pump coupled in fluid communication with the reservoir and including a slide defining an axially-elongated passageway and a piston slidably received within the axially-elongated passageway. The slide defines within the axially-elongated passageway a compression zone, a first portion formed between the compression zone and the reservoir, and a second portion located on an opposite side of the compression zone relative to the first portion. The first portion is defined by a first radius and the compression zone is defined by a second radius that is less than the first radius. At least one of the piston and slide is movable relative to the other between (i) a first actuated position with the tip of the piston received within the first portion of the slide, and the compression zone coupled in fluid communication with the reservoir for receiving fluid therefrom, and (ii) a rest position with a tip of the piston received within the second portion of the slide.

A nozzle of the dispenser includes an annular, axially-extending valve seat, an outlet aperture coupled in fluid communication between the valve seat and the compression zone, and a flexible valve cover extending about the valve seat and forming an annular, axially-extending interface therebetween. The interface is connectable in fluid communication with the outlet aperture, and at least part of the valve cover is movable between (i) a normally closed position with the valve cover engaging the valve seat to close the interface and form a fluid-tight seal therebetween, and (ii) an open position with at least part of the valve cover spaced away from the valve seat in response to fluid flowing through the outlet aperture at a pressure greater than a valve opening pressure to allow the passage of pressurized fluid therebetween.

A spring is drivingly connected to the at least one of the piston and slide. The spring drives at least one of the piston and the slide from the loaded to the rest position to pressurize fluid in the compression zone and, in turn, dispense a metered dosage of fluid through the valve and into a user's eye. The valve seat is defined at least in part by a third radius that is greater than the second radius of the compression zone to release the metered dosage through the nozzle at a relatively low velocity and into the user's eye.

BRIEF DESCRIPTION OF THE DRAWINGS

FIG. 1 is a cross-sectional view of a delivery device in a first actuated position with the tip of the piston received within the first portion of the slide, and the compression zone coupled in fluid communication with the reservoir for receiving fluid therefrom.

FIG. 2 is a cross-sectional view of the delivery device of FIG. 1 in a second actuated position with the piston tip located in the compression zone to pressurize a metered dosage of fluid and dispense same through the nozzle tip.

FIG. 3 is a cross-sectional view of the delivery device of FIG. 1 showing the piston tip in the rest position with the outlet aperture of the nozzle in fluid communication with the fluid reservoir and the valve in the normally-closed position.

FIG. 12 is a perspective, cross-sectional view of the delivery device of FIG. 11.

FIGS. 13A through 13C are cross-sectional views of another delivery device that includes a syringe-like plunger rather than a flexible inner bladder to define the variable-volume storage chamber, and showing the plunger in different positions.

FIG. 20 is a perspective view of the housing of FIG. 19.

DETAILED DESCRIPTION OF THE PREFERRED EMBODIMENTS

Figure 4:
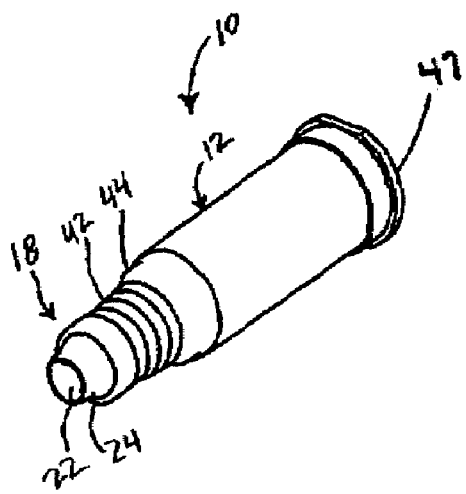
FIG. 4 is a perspective view of the delivery device of FIG. 1.

Referring to FIGS. 1-5, an exemplary embodiment of a delivery device or dispenser is indicated generally by the reference numeral 10. The delivery device 10 comprises a rigid vial or body 12, a flexible bladder 14 mounted within the rigid vial 12, and a storage chamber or reservoir 16 formed between the vial and bladder for receiving therein a fluid or other substance, such as a medicament. The delivery device 10 further comprises a dispensing nozzle 18 and a pump 20 coupled in fluid communication between the dispensing nozzle 18 and the storage chamber 16 for pumping metered doses of the fluid or other substance from the storage chamber 16 through the dispensing nozzle.

The dispensing nozzle 18 includes a relatively rigid valve seat 22 and a flexible, visco-elastic valve cover 24 mounted over the valve seat and defining an axially elongated, annular seam or interface 26 therebetween. As described further below, the pump 20 forces a metered dose of fluid or other substance at sufficient pressure to open the valve (the "valve opening pressure") and force the fluid through the valve interface 26 and out of the delivery device. The valve cover 24 preferably forms an interference fit with the valve seat 22 to thereby form a fluid-tight seal in the normally closed position and, in turn, maintain the fluid or other substance within the delivery device in a sterile and hermetically sealed condition. Further, as shown typically in FIG. 1, the valve cover 24 defines a substantially tapered cross-sectional shape moving in the axial direction from the interior toward the exterior of the valve. This configuration requires progressively less energy to open each respective annular portion of the valve when moving axially from the interior toward the exterior of the valve. As a result, once the base of the valve is opened, the pressure is sufficient to cause the respective axial segments of the valve cover 24 to progressively open and then close after passage of fluid therethrough when moving in the axial direction to dispense a metered dose. Also, during dispensing of a metered dose, preferably a substantially annular segment of the valve cover 24 substantially always engages the valve seat 22 to maintain the fluid-tight seal across the pump 20 and thereby prevent ingress through the valve of germs, bacteria or other unwanted substances into the storage chamber.

The pump 20 includes a rigid slide 28 defining therein an axially elongated bore 30. A piston 32 is slidably received within the bore 30 and includes a piston tip 34 on the free end thereof. The piston 32 and tip 34 define a fluid conduit 36 extending therethrough. A dosage chamber 38 is formed between the piston tip 34 and a stop surface 33 formed on the axially inner side of the valve seat 22. The fluid conduit 36 is coupled in fluid communication between the dosage chamber 38 and storage chamber 16 for dispensing fluid from the storage chamber into the dosage chamber upon actuation of the pump.

Figure 5:
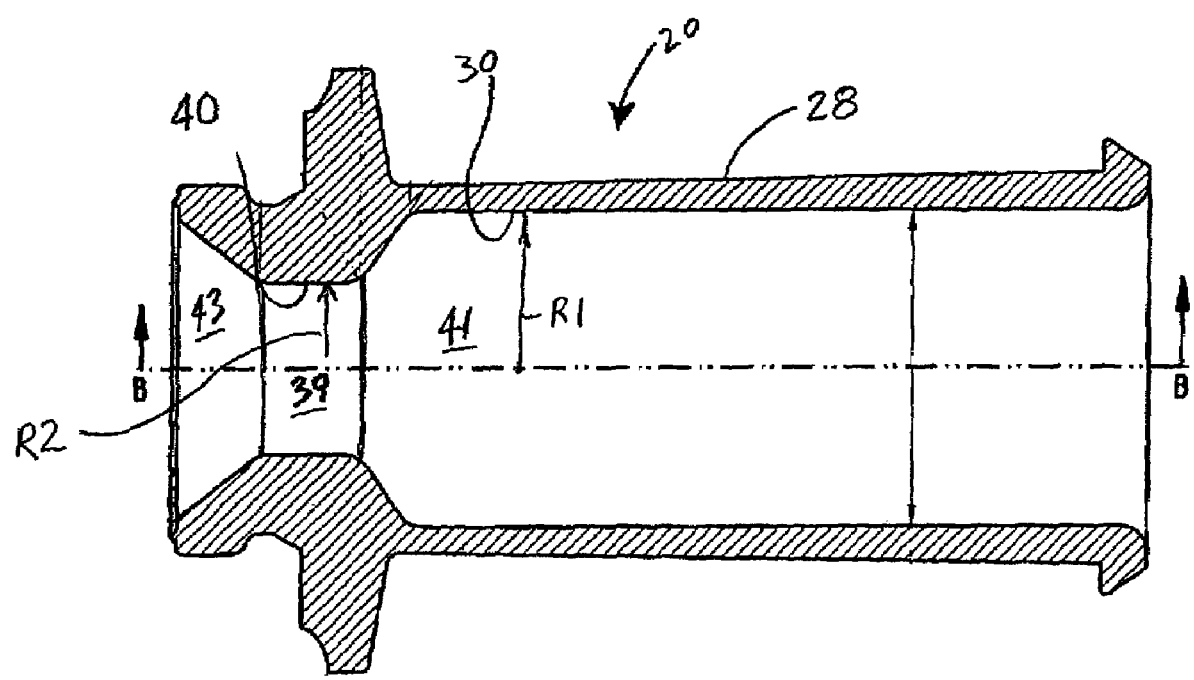
FIG. 5 is a cross-sectional view of the slide of the delivery device of FIG. 1.
Figure 6A:
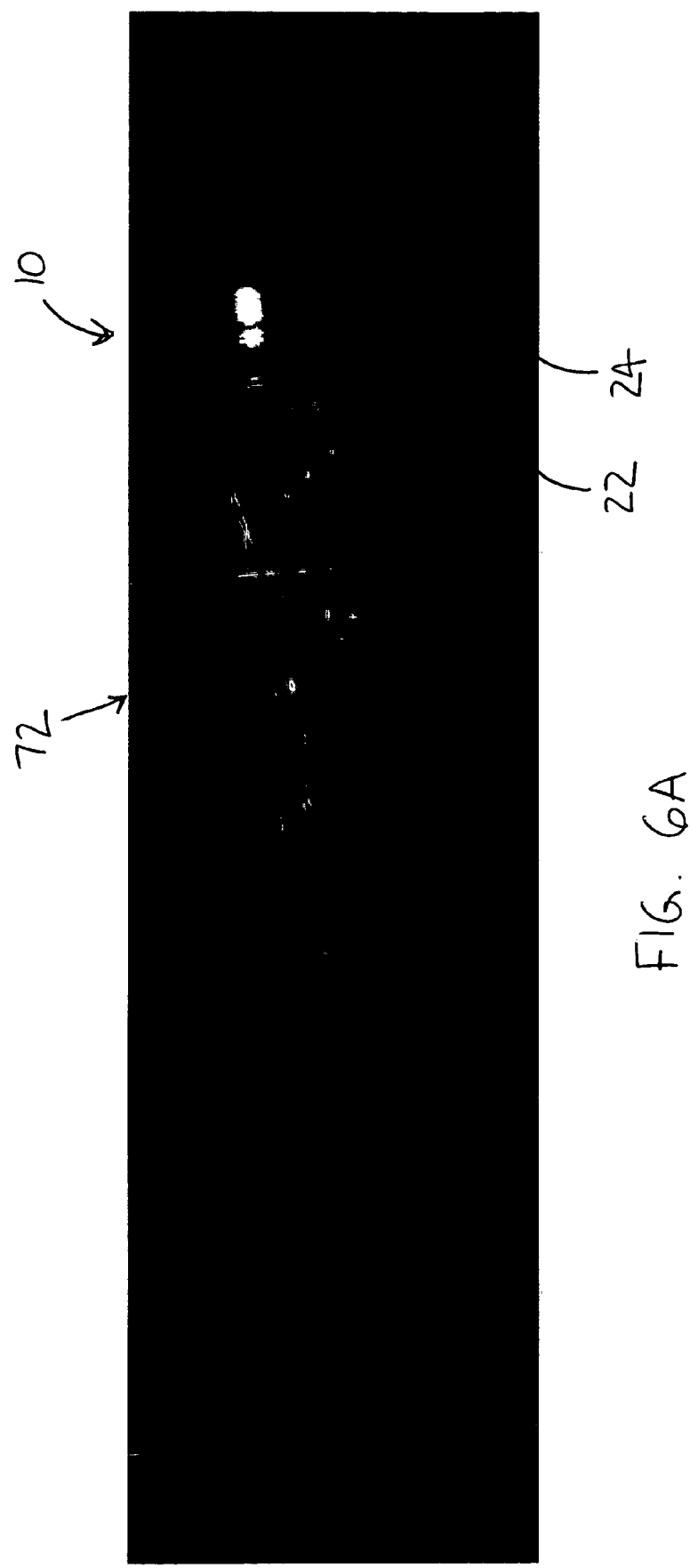
FIG. 6A is a copy of a photograph illustrating an exemplary spray pattern or plume representing a portion of a metered dosage of fluid dispensed from the nozzle of the delivery device at a first point in time.
Figure 6B:
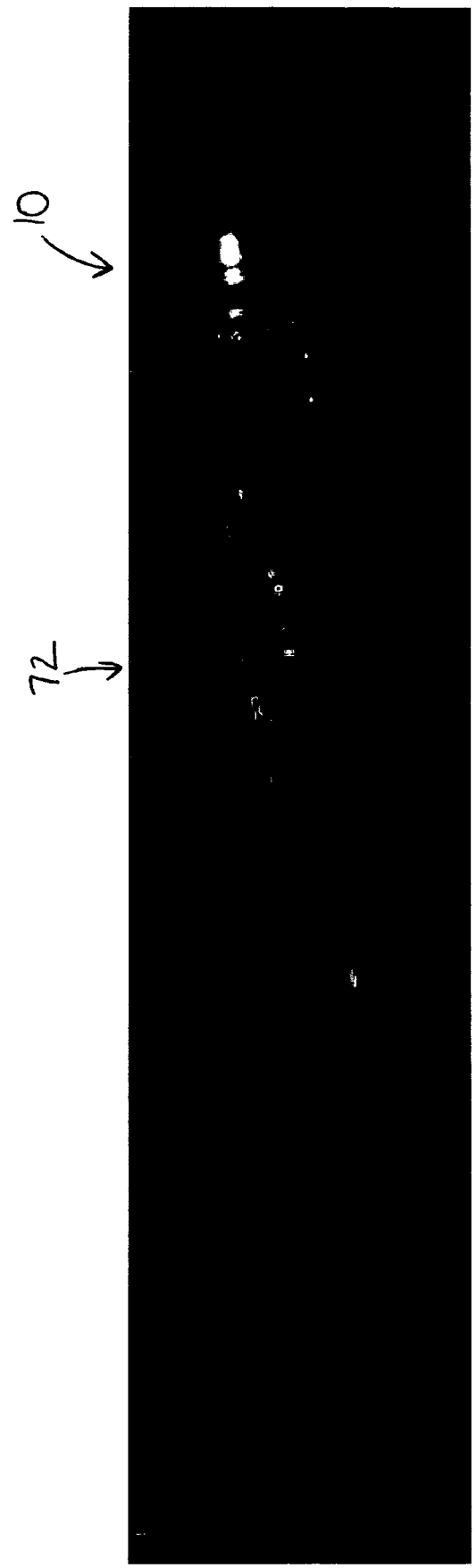
FIG. 6B is a copy of a photograph illustrating an exemplary spray pattern or plume of fluid representing a second portion of the metered dosage of FIG. 6A dispensed from the nozzle of the delivery device at a second point in time subsequent to the point in time of FIG. 6A.
Figure 6C:
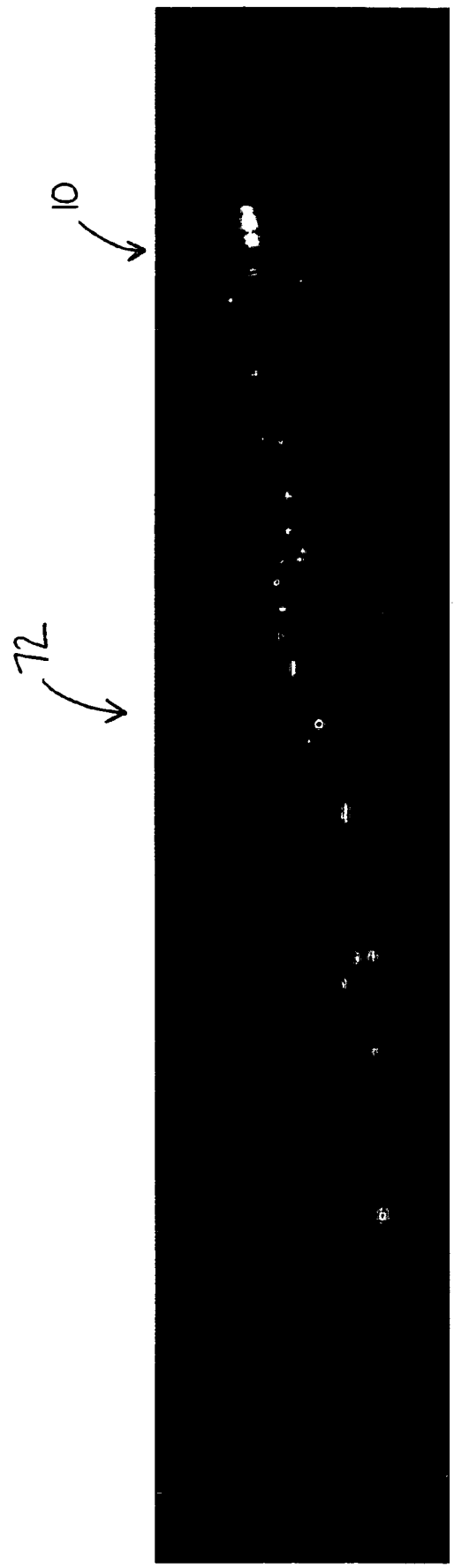
FIG. 6C is a copy of a photograph illustrating an exemplary spray pattern or plume of fluid representing a third portion of the metered dosage of FIG. 6A dispensed from the nozzle of the delivery device at a third point in time subsequent to the point in time of FIG. 6B.

As shown best in FIGS. 1 and 5, the slide 28 defines a reduced cross-sectional portion 40 that cooperates with the piston tip 34 to define the volume of the dosage chamber 38 and thus the dosage volume of the delivery device. The axial extent of the reduced cross-sectional portion 40 defines a compression zone 39 within which the fluid or other substance is compressed by the piston 32 and, in turn, forced through the dispensing nozzle 18. Thus, the slide 28 defines within its axially-elongated passageway the compression zone 39 formed within the reduced cross-sectional portion 40, a first portion 41 formed between the compression zone 39 and the reservoir 16, and a second portion 43 located on an opposite side of the compression zone 39 relative to the first portion 41. The first portion 41 is defined by a first radius "R1", and the compression zone 39 is defined by a second radius "R2" that is less than the first radius R1.

Referring to FIGS. 1-3, the piston 32 is movable relative to the slide 28 (or vice-versa, if desired) between (i) a first actuated position, as shown typically in FIG. 1, with the sealing surface of the tip 34 of the piston 32 received within the first portion 41 of the slide, and the compression zone 39 coupled in fluid communication with the reservoir 16 for receiving fluid therefrom, and (ii) a rest position shown in FIG. 3 with the tip 34 of the piston 32 received within the second portion 43 of the slide. Between the first actuated position (FIG. 1) and the rest position (FIG. 3), there is also a second actuated or seal position (FIG. 2) in which the tip 34 contacts reduced cross-sectional portion 40 to seal the dosage chamber 38.

In the first actuated position (FIG. 1) and on the downward stroke of the piston 32 (i.e., in the direction from the reservoir toward the nozzle), the compression zone 39 is in fluid communication with the fluid conduit 36 and reservoir 16, and thus the fluid is permitted to flow both forwardly in front of the piston, and rearwardly back over the sides of the piston tip 34. Then, when the sealing surface of the piston tip 34 moves into the second actuated position shown in FIG. 2 and slidably engages the reduced portion 40, a fluid-tight seal is formed therebetween, trapping a precise volume of fluid within the compression zone 39 and forcing a precise volume of fluid through the valve. Thus, the piston 32 is moveable relative to the slide 28 (or vice-versa, if desired) from (i) the rest position with the piston tip 34 located in the second portion 43 of the slide as shown in FIG. 3; (ii) to a first actuated position with the piston tip 34 located in the first portion 41 of the slide and the compression zone 39 coupled in fluid communication with the reservoir 16 for receiving fluid therefrom (an exemplary first actuated position is shown in FIG. 1); (iii) to a second actuated position shown in FIG. 2 with the peripheral sealing surface of the piston tip 34 located in the compression zone 39, a fluid tight seal formed between the piston tip and compression zone to pressurize the fluid in the compression zone to a pressure greater than the valve opening pressure and, in turn, cause the pressurized fluid to open the valve and dispense through the valve; and (iv) to the rest position shown in FIG. 3 with the piston tip 34 located in the second portion 43 of the slide and an outlet aperture 45 coupled in fluid communication with the reservoir to reduce the pressure between the outlet aperture 45 and compression zone 39 and allow closure of the valve.

The valve seat 22 defines the outlet aperture 45 extending between the dosage chamber 38 and the interface 26 to allow the fluid to flow therethrough and out of the valve. As described further below, the illustrated embodiment of the present invention includes a single, angular extending outlet aperture 45 for delivering the metered dosage into a conjunctiva cul-de-sac. The valve tip 34 is preferably made of an elastomeric material or a visco-elastic material that is relatively soft in comparison to the slide 28 and reduced portion 40 thereof. For example, the valve tip 34 may be made of a polymeric material, such as the material sold under the trademark Kraton™, or a vulcanized rubber or other polymeric material. As may be recognized by those of ordinary skill in the pertinent art based on the teachings herein, these materials are only exemplary, however, and numerous other materials that are currently or later become known for performing the function of the valve tip equally may be used.

A spring portion or bellows 42 is formed integral with the valve cover 24 and extends between the base of the valve cover and the vial 12. As can be seen, the piston 32 is formed integral with the vial 12 and extends axially therefrom. The spring 42 is fixedly secured at one end to the vial 12 at a first annular flange 44, and is fixedly secured at another end to a second annular flange 46 extending outwardly from the base of the valve seat 22. The pump 20 is actuated by moving at least one of the piston 32 and slide 30 relative to the other to cause the piston tip 34 to move axially within the slide to load the dosage chamber 38 and, in turn, dispense the metered dose of fluid or other substance from the dosage chamber and through the valve.

As may be recognized by those of ordinary skill in the pertinent art based on the teachings herein, the construction of many aspects of the delivery device 10, including aspects of the vial, flexible bladder, pump and nozzle, may be the same as described in co-pending U.S. patent application Ser. No. 10/001,745, filed Oct. 23, 2001, entitled "Fluid Dispenser Having A Rigid Vial And Flexible Inner Bladder", which is assigned to the Assignee of the present invention, and is hereby expressly incorporated by reference as part of the present disclosure. In addition, the delivery device 10 may be mounted within any of the cartridges and/or housings shown in U.S. Patent Application Ser. No. 60/420,334, filed Oct. 21, 2002, entitled "Dispenser", and/or U.S. Patent Application Ser. No. 60/443,524, filed Jan. 28, 2003, entitled "Dispenser", and U.S. patent application Ser. No. 10/691,270, filed Oct. 21, 2003, entitled "Ophthalmic Dispenser and Associated Method", all of which are assigned to the Assignee of the present invention, and are hereby expressly incorporated by reference as part of the present disclosure.

Moreover, this patent application is related to the co-pending U.S. patent application Ser. No. 10/691,270, filed Oct. 21, 2003, entitled "Ophthalmic Dispenser and Associated Method", U.S. Patent Application Ser. No. 60/539,603, filed Jan. 27, 2004, entitled "Dispenser Having Variable Volume Storage Chamber", U.S. application Ser. No. 10/843,902, filed May 12, 2004, entitled "Dispenser and Apparatus and Method for Filling a Dispenser", and U.S. application Ser. No. 10/893,686, filed Jul. 16, 2004, entitled "Piston-Type Dispenser with One-Way Valve for Storing and Dispensing Metered Amounts of Substances", all of which are hereby expressly incorporated by reference as part of the present disclosure.

The delivery device 10 further comprises an end cap 47 including a mounting flange 79 that is received within the open end of the vial 12 and fixedly secured thereto, a filling tube 50 extending axially inwardly from the flange 79 and defining a fluid conduit 52 therein, and a substantially dome-shaped valve seat 54 formed at the other end of the filling tube and engaging the base of the bladder 14. The flexible bladder 14 defines an annular sealing flange 51 that is compressed between the flange 79 of the end cap 47 and the vial 12 to form a fluid-tight seal therebetween. The flange 79 of the cap 47 defines axial spaced peripheral lobes 88 that are snap-fit into corresponding annular recesses 89 of the vial to fixedly secure the cap to the vial with the sealing flange 51 of the bladder compressed therebetween.

The bladder 14 and dome-shaped valve seat 54 cooperate to form a second or filling valve 56. The filling valve 56 includes a valve member 58 formed integral with the bladder 14, and a substantially dome-shaped spring portion 60 also formed integral with the bladder 14 and extending between the valve member 58 and a base portion 62 of the bladder. At least one valve aperture 64 is formed through the dome-shaped valve spring 60 to permit the flow of fluid and/or other substance therethrough when the filling valve is in the open position. The flexible valve member 58 defines a first sealing surface 66 that sealingly engages the valve seat 54 in the normally-closed position to form a fluid-tight seal therebetween. The spring 60 normally urges the valve member 58 axially outwardly (left to right in the Figure) to cause the first sealing surface 66 to sealingly engage the valve seat and form a fluid-tight seal therebetween. The spring 60 allows the flexible valve member 58 to be moved axially inwardly (right to left in the Figure) to, in turn, open the valve and allow the flow of fluid or other substance therethrough. The valve member 58 defines on its interior side a second sealing surface 68, and the vial 12 defines at the inlet to the fluid conduit 36 a corresponding annular valve seat 70. In the open position of the filling valve 56, the second sealing surface 68 may be moved into engagement with the valve seat 70 to form a fluid-tight seal therebetween to, in turn, prevent the flow of fluid into the fluid conduit 36 of the piston.

The bladder 14 (including the integral valve member 58) is preferably made of an elastomeric material or visco-elastic material that is relatively soft in comparison to the vial 12 and valve seat 54. For example, the bladder 14 may be made of a polymeric material, such as the material sold under the trademark Kraton™, or a vulcanized rubber or other polymeric material. However, as may be recognized by those of ordinary skill in the pertinent art based on the teachings herein, these materials are only exemplary, and numerous other materials that are currently, or later become known for performing the functions of the bladder and/or valve member equally may be used. The filling valve, filling assembly and method of filling are described in further detail in the co-pending patent applications incorporated by reference above.

As shown in FIG. 1, when the delivery device is empty, the bladder 14 is fully expanded into engagement with the interior surfaces of the vial 12 such that the variable volume storage chamber 16 is at substantially zero volume. As described in the above-mentioned co-pending patent applications, the bladder 14 is preferably formed such that it naturally tends to flex outwardly and create a positive pressure gradient on the fluid or other substance in the storage chamber 16. Also, in this position, the valve member 58 of the filling valve 56 is in the normally closed position to maintain the interior of the delivery device hermetically sealed. In this condition, the empty delivery device may be sterilized prior to filling, such as by applying gamma, e-beam, or another type of radiation thereto. Then, the sealed, empty and sterilized delivery device 10 may be transported to a sterile filling machine or other filling station without risk of contaminating the sterilized interior portions of the delivery device, as described further below.

In order to fill the delivery device 10 with a fluid or other substance from the fluid source (not shown), the tip of a filling member (not shown) is moved axially inwardly against the valve member 58 of the filling valve 56 to open the valve. Preferably, the valve member 58 is moved axially inwardly until the second sealing surface 68 of the valve member sealingly engages the corresponding valve seat 70 to form a fluid-tight seal therebetween. Then, fluid is introduced from a fluid source, through the filling member and open filling valve 56 and into the storage chamber 16. The base 62 of the bladder 14 defines one or more grooves 71 or like fluid passageways formed between the base of the bladder 14 and vial 12, and extending in fluid communication between the inlet aperture 64 of the filling valve and storage chamber 16. In the fully open position, the second sealing surface 68 and corresponding valve seat 70 prevent fluid from flowing into the piston, and thus prevent such fluid from flowing into the valve 18 during the filling process. The fluid is filled into the storage chamber 16, the bladder 14 collapses and the variable volume chamber 16 correspondingly expands. In the filled position, the bladder 14 is collapsed toward, or in contact with, the fill tube 50. Once the storage chamber is filled, the filling member is moved out of the fill tube 50 and the spring 60 of the filling valve 56 closes the valve member 58 to hermetically seal the fluid or other substance within the storage chamber 16 of the delivery device. Upon withdrawing the filling member and closure of the filling valve 56, the fluid or other substance within the storage chamber 16 is drawn into the formerly evacuated space of the piston conduit 36. As a result, the pump 20 will require at most minimal priming prior to dispensing the first dose of fluid or other substance therefrom.

In sum, the sealed, empty, sterilized delivery devices 10 are introduced into a filling machine of the type disclosed in the above-mentioned co-pending patent applications. Alternatively, if desired, the sealed, empty delivery devices may be sterilized within the filling machine, such as by applying gamma and/or e-beam radiation thereto in a first stage of the sterile filling machine. In the filling machine, the delivery devices are first evacuated in a vacuum station. Then, the sealed, evacuated delivery devices are filled in a filling station (both the vacuum and filling stations preferably include laminar flow to maintain aseptic conditions, as described above). If deemed necessary or desirable, an e-beam or other radiation source may be used to sterilize the exposed surface of the valve member 58 to further ensure sterilization of this surface prior to engagement of the surface with the evacuating/filling member. For example, the evacuating and/or filling stations may be located within an e-beam chamber similar to the manner in which a needle filling station is located within an e-beam chamber as disclosed in co-pending U.S. patent application Ser. No. 10/600,525, filed Jun. 19, 2003, entitled "Sterile Filling Machine Having Needle Filling Station Within E-beam Chamber", which is assigned to the Assignee of the present invention and is hereby expressly incorporated by reference as part of the present disclosure. Alternatively, a laser or other radiation source may be employed to scan or otherwise subject the exposed surface of the valve member 58 to radiation prior to passage through the evacuation and/or filling stations to further ensure the sterility of such surfaces.

The filled, sterilized, and hermetically sealed delivery devices are discharged from the sterile filling machine and ready for usage.

As can be seen, the illustrated embodiment of the present invention implements the following features:

1. The valve seat 26 diameter is greater (in comparison to the compression zone 40 diameter) in order to decrease the valve opening pressure (and concomitantly allow an increase in the cross-sectional surface area of the valve outflow hole 45).
2. When the piston tip 34 is driven from the first actuated into the second actuated position (i.e., into a peripherally sealed position in the compression zone 40), a relatively large volume of fluid is rapidly displaced by the piston. If the valve opening pressure is too low, there is a risk that the valve will open prior to forming a peripheral seal between the piston tip and compression zone. If this occurs, the dosage volume may not be precisely controlled. In order to ensure that this does not occur, in the illustrated embodiment, the head loss in the forward direction of the piston tip (i.e., in the direction from the piston tip toward the outlet aperture 45) is greater than the head loss in the rearward direction of the piston tip (i.e., in the direction from the piston tip toward the storage chamber 16). In the illustrated embodiment, the diameter or cross-sectional area of the inlet point “A” of the outflow aperture 45 is formed sufficiently small to create the requisite head loss differential to ensure that the forward head loss is greater than the rearward head loss.
3. The outlet opening 45 of the valve is oriented at an oblique angle in order to reduce the head loss through the outlet opening 45 and thereby reduce the pressure required to dispense the metered dosage through the valve (i.e., achieve a low valve opening pressure). In addition, the diameter or cross-sectional area of the inlet point “A” of the outlet aperture 45 is less than the diameter or cross-sectional area of the outlet point “B” of the outlet aperture 45 in order decrease the velocity of the fluid flowing in the direction from point A to point B, and, in turn, reduce the drop velocity in comparison to prior dispensing devices.
4. In addition, the cross-sectional surface area of the nozzle at point B of the outflow aperture is maximized in relation to the cross-sectional surface area of the compression zone 40 in order to minimize the pressure gradient between the compression zone and the atmosphere and, thus, due to the law of conservation of energy, reduce the drop velocity in comparison to prior dispensing devices. In other words, the drop velocity is approximately proportional to the ratio of the cross-sectional area of the compression zone 40 to the cross sectional area of the valve seat at point B of the outflow hole. In sum, the delivery device enables a dosage velocity similar to the piston velocity or even lower, and the piston velocity can be precisely controlled by controlling the force of the spring or springs driving the piston, or driving relative movement of the piston and compression zone.

5. In particular, each drop can be controlled to deliver a volume within a range of about 15 to about 25 micro liters, and more preferably in the range of about 17 to about 22 micro liters, with each dose being delivered at plus or minus about 5% of the registered or designated volume. This volume of drop allows a maximum amount of fluid to be delivered to an eye without overflowing the cul-de-sac of the eye. This volume of drop also allows the fluid to be delivered without losing visual acuity after the drop is administered to the eye.
6. By controlling the dosing amount, the device allows for an effective manner in the treatment of dry eye. Specifically, by utilizing the device a dose is administered in the range of about 15 to about 25 micro liters to the ocular cul-de-sac. The dose is then administered four times each day, which equals the approximate amount of an average person’s tear production. Accordingly, due to the controlled amount of dosage, and the fact that the maximum amount of fluid is being delivered to the eye without overflowing the cul-de-sac of the eye, the delivery device provides an effective manner in which to treat dry eye.
7. In addition each dose is delivered at a low velocity, which is defined as being low enough so that the user’s eye does not receive an impact that could injure the eye. At the same time, if the velocity of the drop is too low than the drop does not have enough force to leave the nozzle and enter a user’s eye. Accordingly, an exemplary embodiment of a low velocity is defined as a velocity that is less than about 10 meters per second, and with a preferred range of about 2 meters per second to about 6 meters per second, and with a further preferred range of about 2 meters per second to about 4 meters per second.

In order to deliver the dose at a low velocity, the valve seat 22 and the valve cover 24 are configured to dispense the dosage of fluid through the interface 26 at a velocity of equal to or less than about 10 meters per second. For instance, the cross-sectional size, the length, and/or the shape of the valve seat 22 and the valve cover 24 can be adjusted to change the interface 26, which then controls the velocity as the dosage moves through the interface 26. In addition, the change in the cross-sectional size and/or shape of the valve seat 22 and the valve cover 24 as compared to the dosage chamber 38 would also effect and change the velocity of the dosage. The material of the valve seat 22 and the valve cover 24 can also be changed and adjusted so as to effect the velocity of the dosage. Other changes with respect to configuring the valve seat 22 and the valve cover 24 are also contemplated.

In an exemplary embodiment of the invention, the nozzle and outflow hole shapes, and the interference between the visco-elastic valve cover and valve seat, are constructed in order to dispense each metered dosage in a substantially flat or approximately semi-circular flow pattern that preferably defines a plurality of micro-droplets. For example, as shown typically in FIGS. 6A through 6C, an exemplary plume 72 of micro-droplets dispensed by the delivery device 10 extends through an approximately semi-circular arc that substantially conforms to the angular extent of a conjunctiva cul-de-sac (or other predetermined target shape) such that the plume preferably defines a plurality of micro-droplets that are spaced relative to each other on impact with the conjunctiva cul-de-sac. In addition, the eye-cup or wings, axis of the pump and outflow hole of the delivery device and housing holding the delivery device are set to deliver the plume, including the micro-droplets thereof, onto the conjunctiva cul-de-sac (as opposed to the more sensitive cornea as with prior art eye droppers). Each metered dosage passes between the axially-elongated flexible valve cover and rigid valve seat, and the shearing forces imparted to the fluid cause the metered dosage to be dispensed in the plume including micro-droplets as illustrated, for example, in FIGS. 6A through 6C.

Also in the illustrated embodiment of the invention, the energy imparted by each individual micro-droplet to the conjunctiva cul-de-sac or any other target fragile tissue (e.g., an interior surface of the ear, burn tissue, or the tissue of a lesion)

is substantially similar to or less than the energy imparted by a 30 to 50 micro-liter drop delivered by a traditional eye dropper to the anterior surface of the eye (or other fragile tissue) at conventional delivery distances (1 to 10 cm). As a result, chronic instillation of metered dosages from the delivery device of the invention will create less cellular stress on the relatively non-sensitive surface of the conjunctiva cul-de-sac in comparison to the uncontrolled, larger doses delivered by traditional eye droppers to the more sensitive corneal tissue. For example, each droplet in the plume or fluid spray or delivery pattern of the illustrated delivery device defines a significantly smaller mass than a conventional 30 to 50 micro-liter drop, and therefore delivers significantly less energy upon impact with the eye or other target area. In a further example, the droplets are about 5 microliters, and are delivered at a velocity of about 3 meters per second, and thus the droplet imparts less than about 30 micro-joules upon impact with the eye.

Turning to FIGS. 7 through 10, another exemplary embodiment of the delivery device is indicated generally by the reference numeral 110. The delivery device 110 is shown mounted in a housing 174. It is understood that delivery device 10 may also be mounted in the housing 174 in a similar manner. The delivery device 110 is similar in many respects to the delivery device 10 described above, and therefore like reference numerals preceded by the numeral "1" are used to indicate like elements.

Figure 8:
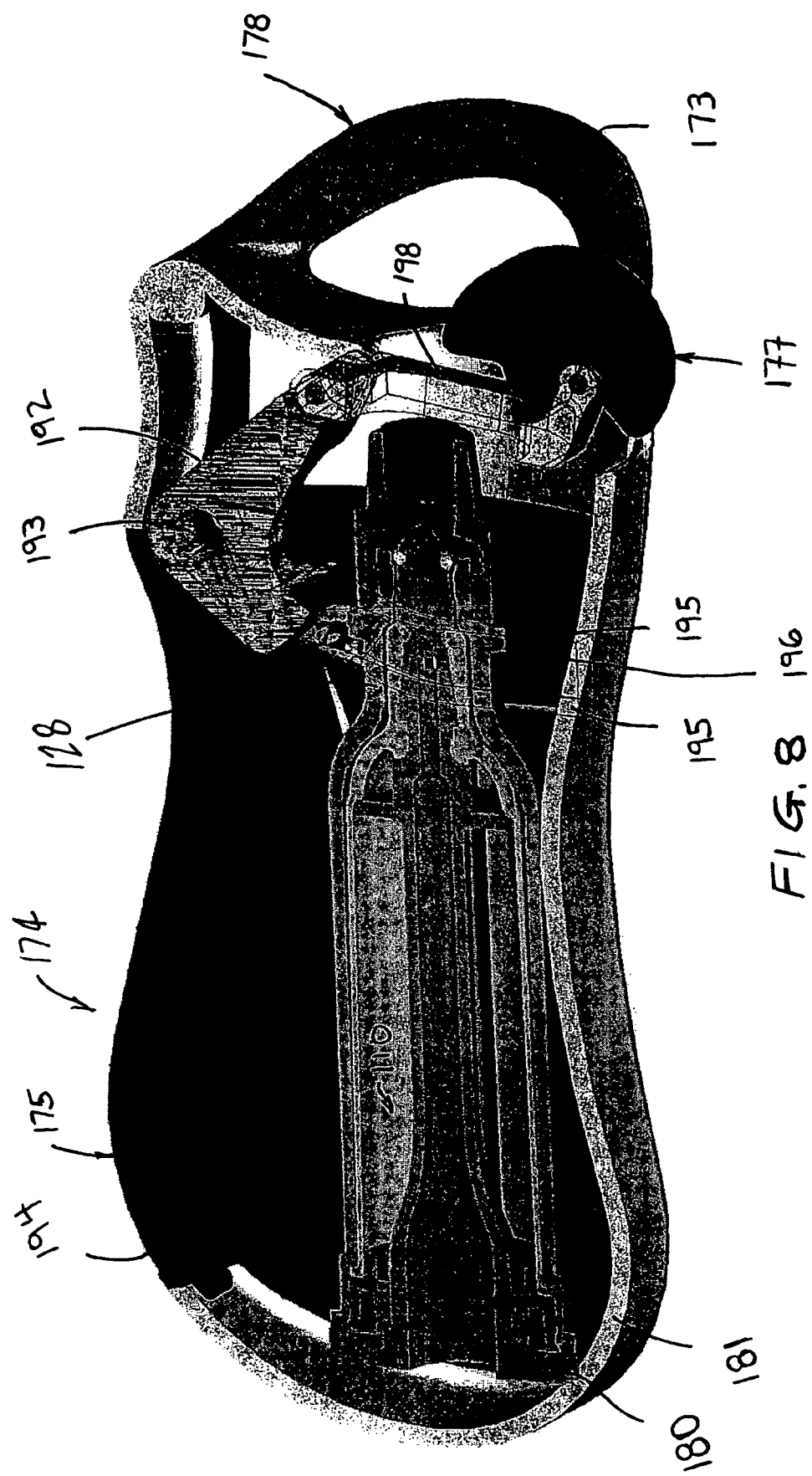
FIG. 8 is a perspective, cross-sectional view of the delivery device and housing of FIG. 7.
Figure 9:
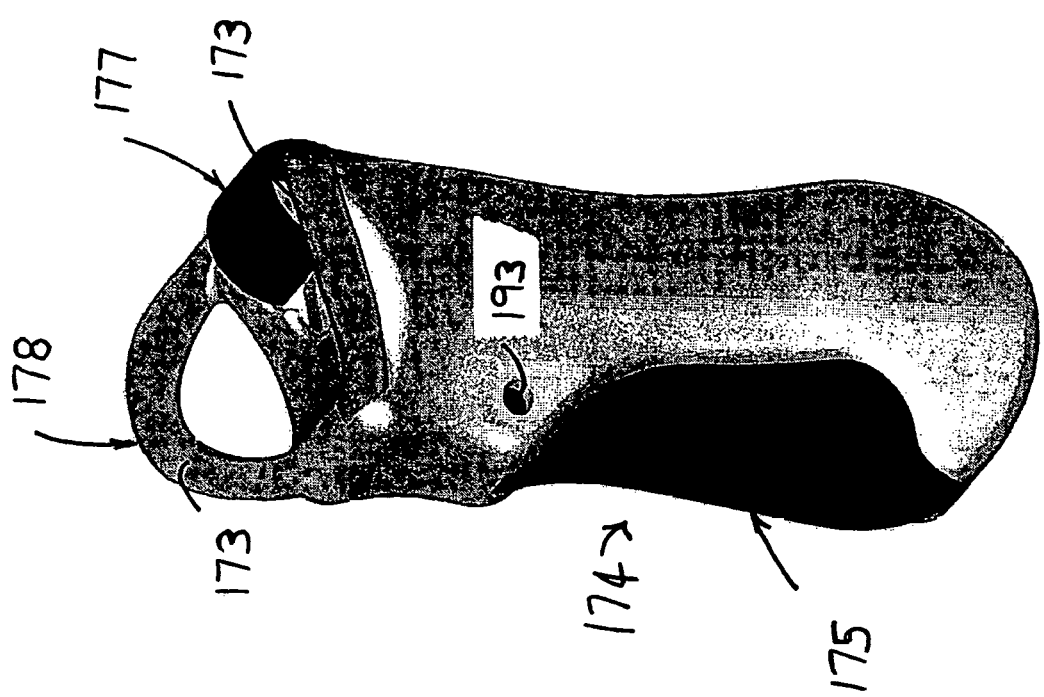
FIG. 9 is a side perspective view of the housing of FIG. 7.
Figure 10:
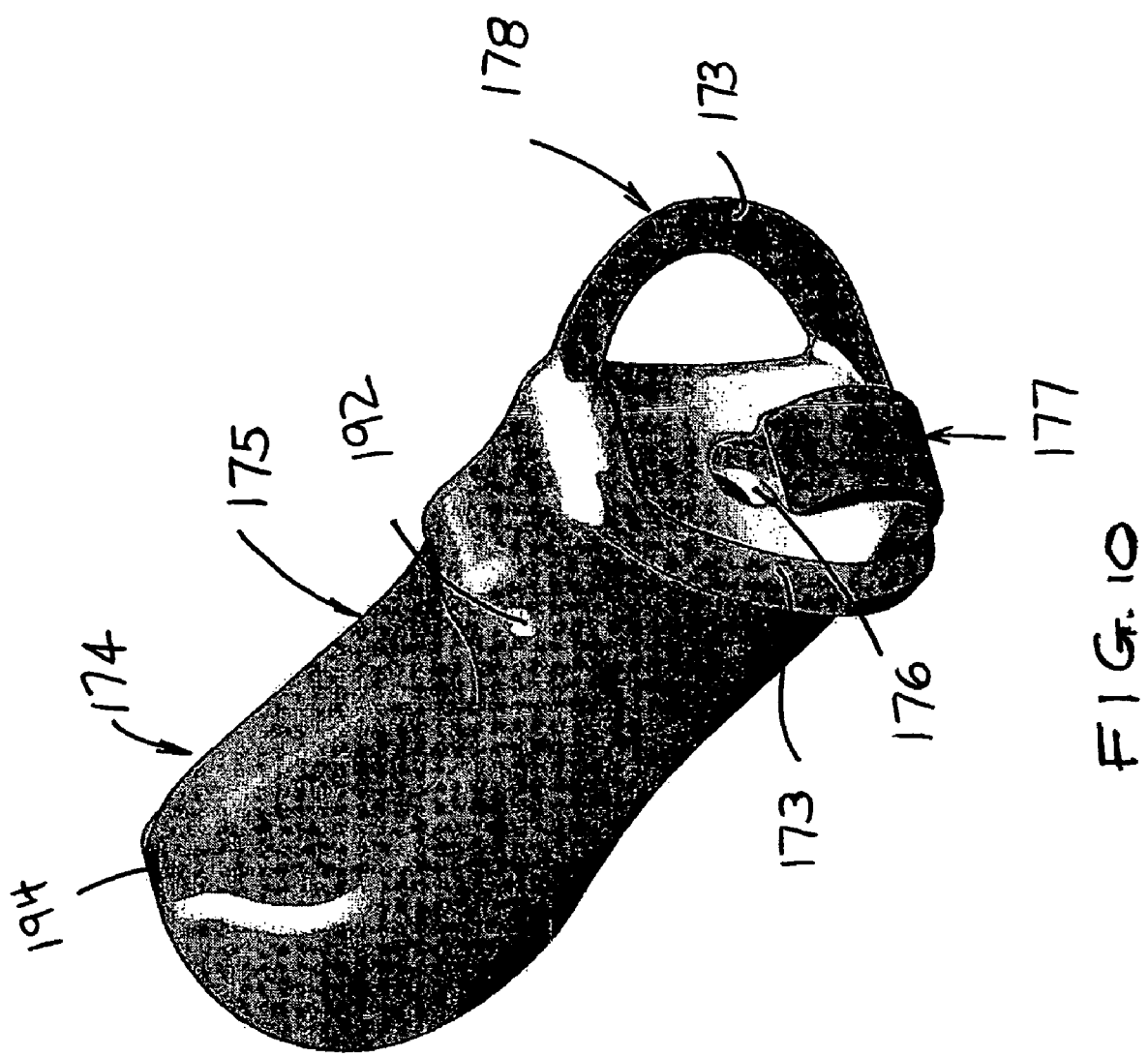
FIG. 10 is an upper perspective view of the housing of FIG. 7.

The delivery device 110 is mounted within the housing 174 including an actuator 175 for actuating the pump 120 of the delivery device; a dispensing aperture 176 aligned with the outlet interface 126 of the nozzle 118 for receiving therethrough a metered dosage of medicament, fluid or other substance from the storage chamber 116; an eye-lid depressor 177 pivotally mounted on the housing adjacent to the dispensing aperture 176 for engaging the facial tissue adjacent to the conjunctiva cul-de-sac and substantially simultaneously exposing the cul-de-sac and dispensing the metered dosage therein; and, as shown in FIGS. 8-10, an eye-cup 178 for engaging the facial tissue adjacent to the eye to properly position the housing and delivery device thereon and direct the metered dosage onto a substantially predetermined portion of the eye, such as the exposed conjunctiva cul-de-sac.

Figure 7:
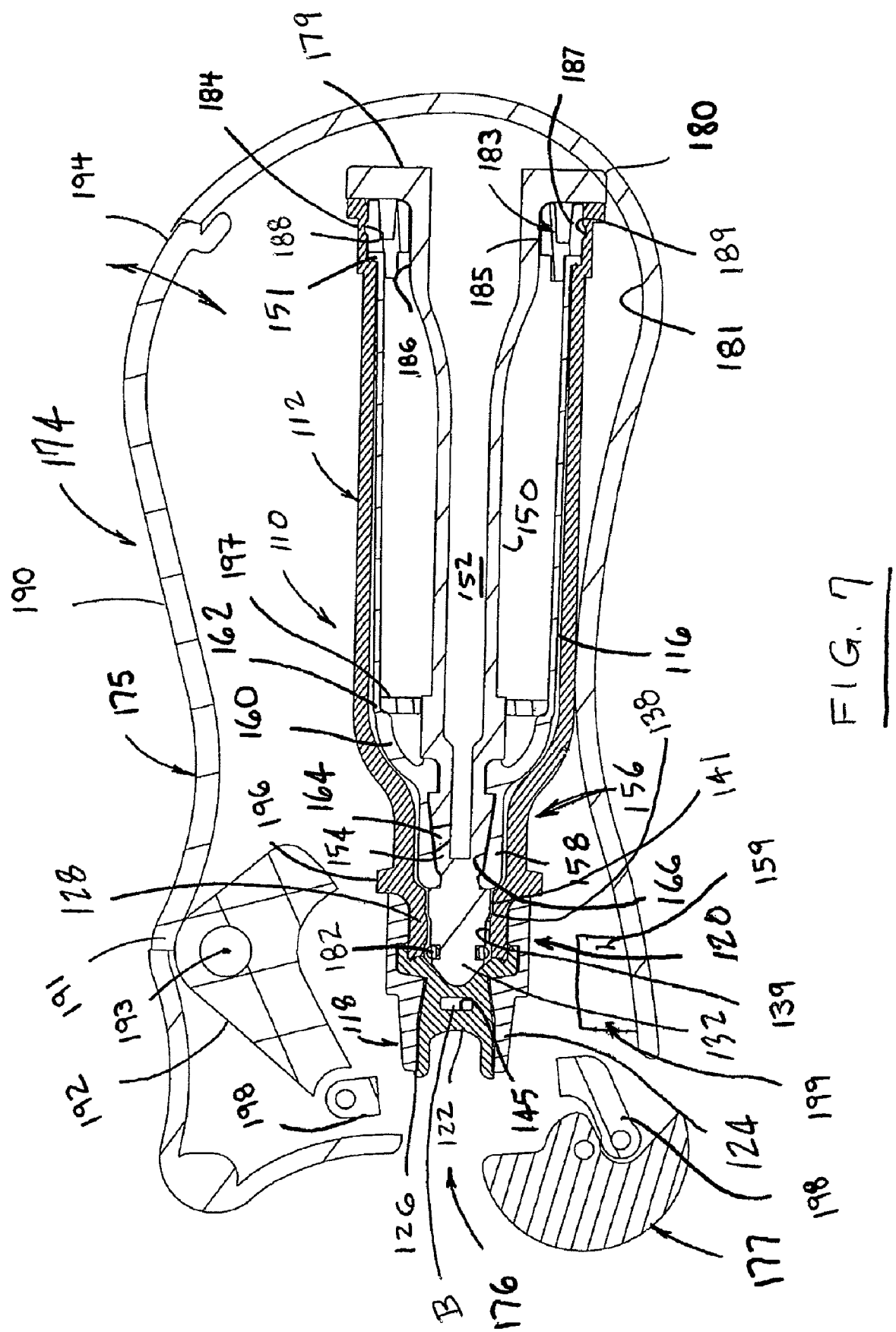
FIG. 7 is a cross-sectional view of another embodiment of a delivery device shown mounted within a housing including an eye-cup, a trigger for actuating the pump, and an eyelid depressor for engaging facial tissue adjacent to the conjunctiva cul-de-sac of an eye to substantially simultaneously expose the cul-de-sac and deliver thereto a metered dosage of medicament or other substance from the delivery device.

As shown in FIG. 7, the flange 179 of the delivery device 110 is fixedly secured at a portion 180 to a base wall 181 of the housing 174. Thus, one of the differences between the delivery device 110 and the delivery device 10 described above, is that the pump 120 is actuated by moving the vial body 112, and the slide 128 formed integral with the vial body, relative to the piston 132, and the piston 132 is formed integral with the fill tube 150 and flange 179. In the illustrated embodiment, the piston 132 is formed of a relative rigid material, such as a thermoplastic or other engineering plastic, and includes an o-ring or like annular sealing member 182 received within a peripheral groove thereof that forms an interference fit with the compression zone 139, and thus a fluid-tight seal therebetween. In one embodiment of the invention, the piston 132 and vial body 112 are formed of materials that are relatively rigid and/or have favorable sorption characteristics with respect to the substance to be contained in the storage chamber 116, and the sealing member 182 is formed of a less rigid material, such as an elastomeric material, that has less favorable sorption characteristics with respect to the substance to be contained in the storage chamber. In this way, substantially all of the surfaces of the piston, slide and vial body can be formed of materials having favorable sorption characteristics to thereby enhance the sorption characteristics of the delivery device 110 with respect to the substance to stored and dispensed therefrom. In one embodiment of the invention, the substance to be contained in the storage chamber 116 is a latanoprost formulation for treating glaucoma, the material forming the piston and vial body is sold under the trademark TOPAZ™, and the material forming the sealing member is sold under the trademark SANTOPRENE™. However, as may be recognized by those of ordinary skill in the pertinent art, these materials are only exemplary, and may be changed as required to meet the needs of a particular application, or otherwise as desired.

Another difference of the delivery device 110 in comparison to the delivery device 10 is that the valve seat 122 tapers outwardly, or defines an increasing diameter in the direction from the interior toward the exterior of the delivery device. The hoop stress applied by the valve cover 124 to the valve seat varies with the square of the diameter of the valve seat such that the stress is greater the smaller the diameter. Thus, in the illustrated embodiment, the stress is higher at the inlet to the interface 126 (i.e., at the outlet point B of the outlet aperture 145) than at the outlet of the interface 126. Accordingly, when the pumped fluid in the compression zone exceeds the valve opening pressure, the fluid that enters the seam will continue to flow through the valve seam and out of the delivery device, rather than backflow from the valve seam into the compression zone, because of the decreasing level of stress at the valve interface when moving in the direction from the interior toward the exterior of the valve. This feature also facilitates ensuring that progressively less energy will be required to open each respective annular segment of the valve when moving axially from the interior toward the exterior of the valve, and therefore facilitates ensuring that once the base of the valve is opened, the pressure will be sufficient to cause the respective axial segments of the valve cover 124 to progressively open and then close after passage of fluid therethrough when moving in the axial direction to dispense a metered dose. If desired, the valve cover 124 may define a tapered cross-sectional shape that tapers inwardly, or may define a progressively decreasing thickness moving in the axial direction from the interior toward the exterior of the valve, as described above, and shown typically in FIG. 7. However, if desired, the valve cover may define a uniform thickness across the valve seat, and may rely only on the outward taper of the valve seat to achieve the desired performance, as described above.

As also shown in FIG. 7, the delivery device 110 further comprises an annular bearing member 183 extending radially between a flange 184 formed on the adjacent end of the vial body 112 and the fill tube 150. The bearing member 183 defines a first annular bearing surface 185, and the fill tube defines a second annular bearing surface 186 received within the first bearing surface 185 and slidable relative thereto. An outer wall 187 of the bearing member is tapered radially outwardly to cause the annular protuberance 188 thereof to be snapped into the corresponding annular groove 189 formed in the flange 184 of the vial body 112 to secure the bearing member to the vial body. Thus, the bearing member 183 and vial body 112 fixedly secured thereto are movable axially relative to the fill tube 150 and flange 179 thereof, to in turn, move the slide 128 and compression zone 139 thereof relative to the piston 132 between the first actuated, second actuated and rest positions, as described above.

The actuator 175 of the housing 174 includes a trigger 190 fixedly secured at a first end 191 to a pivotally mounted drive member 192. As shown typically in FIGS. 7 and 8, the drive member 192 is pivotally mounted to the housing at pivot pin 193. As indicated by the arrows in FIG. 7, a second end 194 of the trigger 190 is movable relative to the wall 181 of the housing to thereby allow a user to engage the outer surface of the trigger and depress the trigger to actuate the pump. As shown in FIG. 8, the drive member 192 includes first and second drive arms 195 that are laterally spaced relative to each other and engagable with an annular flange 196 formed on the outer surface of the slide 128 and extending radially outwardly therefrom. As shown in FIG. 7, the base 162 of the bladder defines a dome spring 160 extending between a base portion of the piston 132, and a stop 197 extends between the base 162 and fill tube 150. A linkage 198 is pivotally coupled between the forward end of the drive member 192 and the eyelid depressor 177 to rotatably drive the depressor and, in turn, engage the lower eyelid to expose the conjunctiva cul-de-sac with actuation of the trigger.

Upon depressing the trigger 190 inwardly toward the delivery device 110, the drive member 192 is pivoted in a clockwise direction in FIG. 7 to, in turn, cause the first and second drive arms 195 thereof to engage the annular flange 196. This, in turn, drives the slide 128 from the rest position shown typically in FIG. 7 to a first actuated position with the tip of the piston 132 received within the first portion 141 of the slide 126, and the compression zone coupled in fluid communication with the reservoir 116 for receiving fluid therefrom. This action also causes the dome spring 160 to compress both axially and radially inwardly, and thereby store sufficient energy to drive the slide in the return stroke. When the slide is located in the first position, the fluid flows from the reservoir 116 into the dosage chamber 138 to fill the chamber. As shown in FIG. 7, the housing 174 includes an engagement block 199 formed at the base of the housing and defining opposing lateral surfaces 159 (only one shown) that engage the drive arms 195 and force the drive arms laterally outwardly with further movement thereof toward the front end of the housing. The inward movement of the trigger also causes the linkage 198 to rotate the eye-lid depressor 177 to lower the eyelid as described above. As the trigger 190 nears the end of its inward stroke, the engagement block 199 releases the drive arms 195 from the annular flange 196 of the delivery device. This allows the radially and axially compressed dome spring 160 to drive the slide 128 and vial body 112 to, in turn, dispense the metered dose. Thus, one advantage of the illustrated embodiment is that the dome spring controls the relative movement of the slide and piston tip to release a dosage, and thus can be substantially precisely set to control, in part, the velocity of the dosage. In addition, placing the pivot pin 193 of the actuator adjacent to the relatively narrow nozzle 118 of the delivery device allows for a compact design, thus permitting the device to be made relatively small to fit, for example, within a shirt pocket or small pocket of a purse or other bag. Further, the relatively long trigger 190 provides substantial torque and/or leverage at the pivot point to permit easy actuation of the delivery device.

As shown in FIG. 7, the base portion of the bladder defines a flexible filling valve member 158 that forms an interference fit with an underlying valve seat 154 of the fill tube. A fill opening 164 extends between the fluid conduit 152 of the fill tube and the valve interface to allow the fluid or other substance to be pumped therethrough to fill the delivery device. This type of filling valve is described in the co-pending patent application incorporated by reference above.

The eye-cup 178 defines opposing facial engaging surfaces 173 that are shaped to conformably contact the tissue adjacent to a user's eye. If desired, these surfaces may be pivotally mounted to the housing 174 to allow them to be folded toward each other when not in use and thereby reduce the lateral profile of the device.

Figure 11:
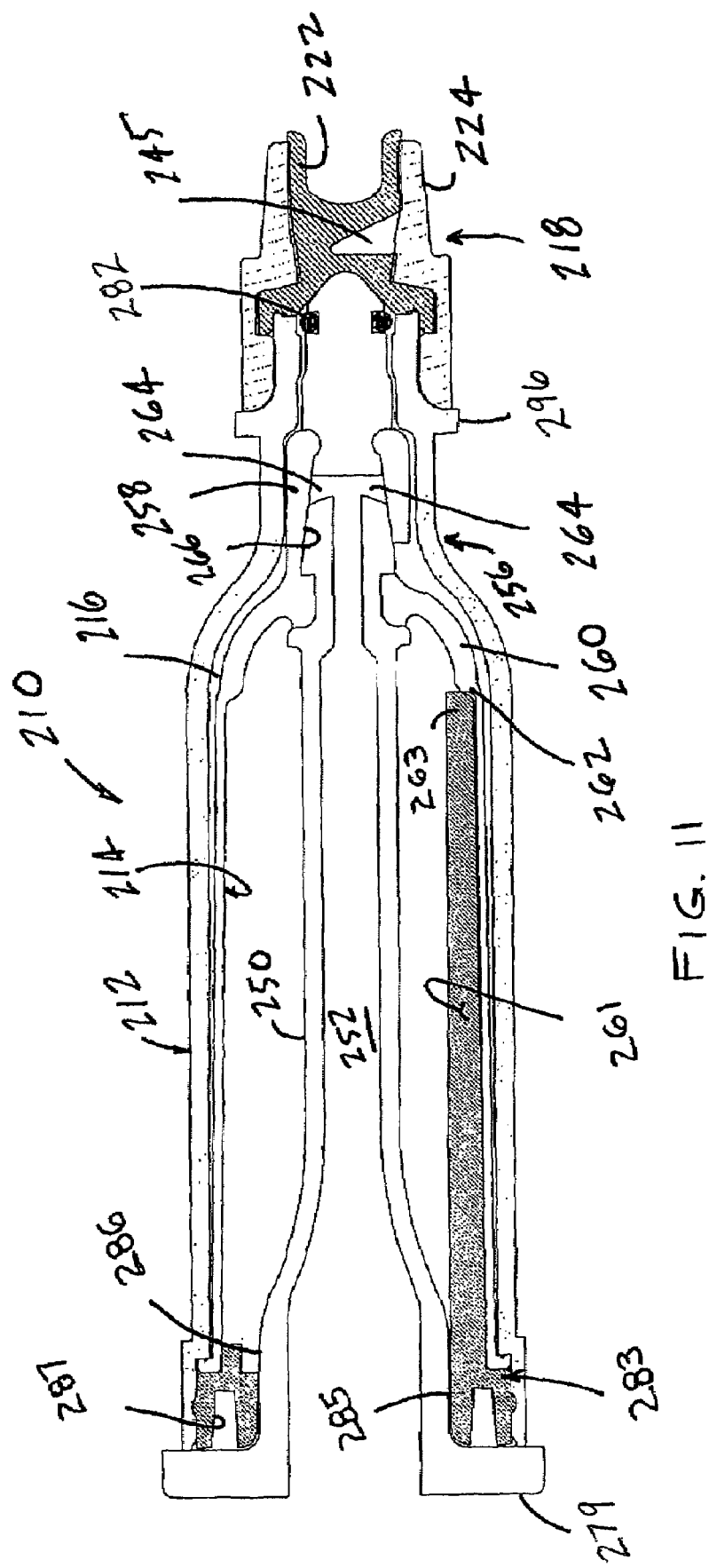
FIG. 11 is a cross-sectional view of another delivery device.

In FIGS. 11 and 12, another delivery device embodying the invention is indicated generally by the reference number 210. The delivery device 210 is substantially similar to the delivery device 110 described above, and therefore like reference numerals preceded by the numeral "2" instead of the numeral "1" are used to indicate like elements. A primary difference of the delivery device 210 in comparison to the delivery device 110 is that the bearing member 283 includes a rigid member 261 that extends axially between the first sealing surface 285 of the bearing member and the base 262 of the flexible bladder 214. As can be seen, the forward end 263 of the member 261 is pressed axially into the dome spring 260 of the bladder to axially and radially compress the spring during the forward stroke of the pump, and the spring in turn drives the rigid member 261 rearwardly on the rearward stroke of the pump.

Figure 14C:
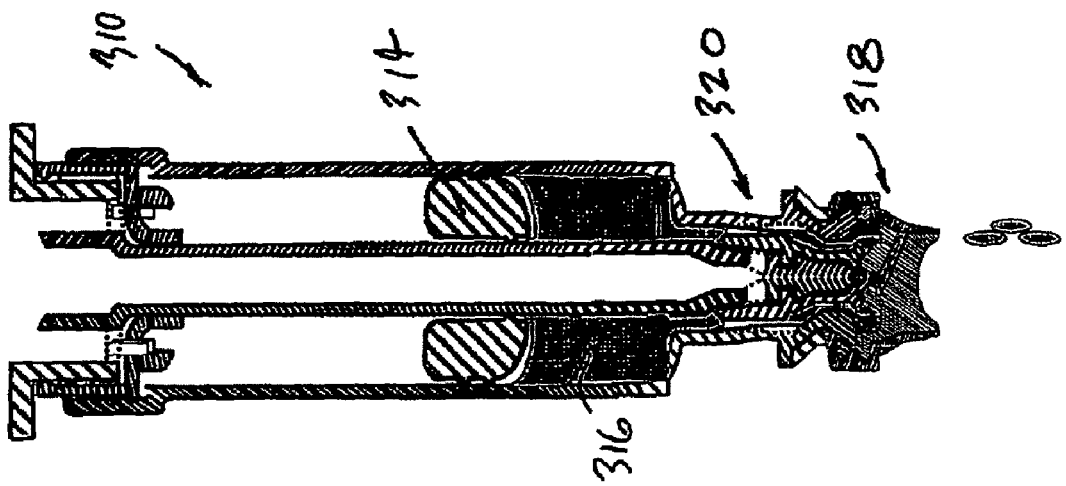
FIGS. 14A through 14C are cross-sectional views of the delivery device of FIGS. 15A through 15C showing the actuation cycle of the delivery device.
Figure 14B:
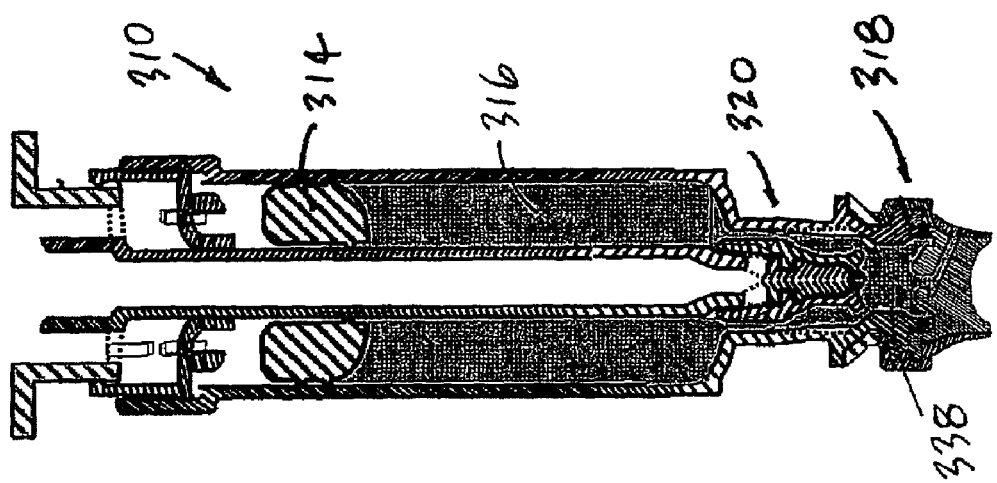
Figure 14A:
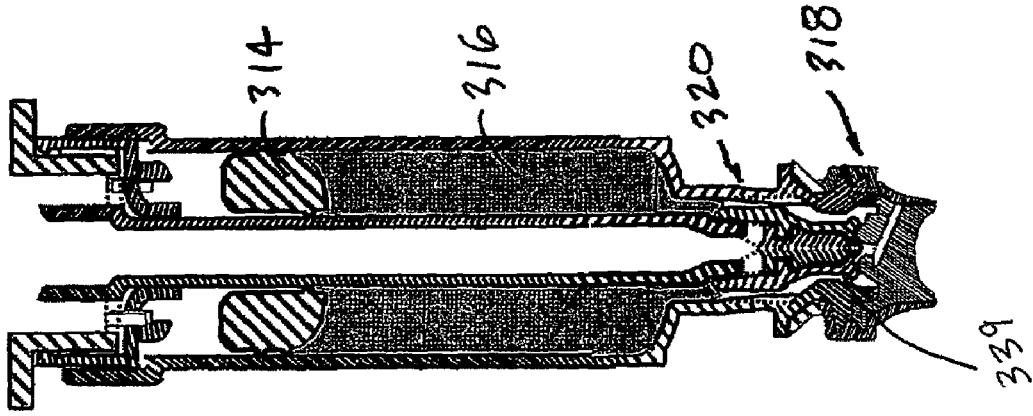

In FIGS. 13A through 14C, another delivery device embodying the invention is indicated generally by the reference numeral 310. The delivery device 310 is similar to the delivery devices 110 and 210 described above, and therefore like reference numerals preceded by the numeral "3" instead of the numerals "1" or "2" are used to indicate like elements. A primary difference of the delivery device 310 in comparison to the delivery device 110 and 210, is that the delivery device 310 does not include a flexible inner bladder. Rather, the delivery device 310 includes an annular plunger 314 that extends between the rigid vial body 312 and the inner fill tube 350. The plunger 314 includes at least one, and preferably two axially spaced, outer annular sealing members 353 that sealingly engage the inner wall of the vial body 312 to form a fluid-tight seal therebetween. The plunger further includes at least one inner annular sealing member 355 that sealingly engages the outer wall of the fill tube 350 and forms a fluid-tight seal therebetween. The sealing members may be formed integral with the plunger, such as by forming thereon annular protuberances, as shown, or may be formed by sealing members, such as o-rings or other sealing members, that are received within corresponding grooves formed in the plunger. As shown in FIGS. 14A through 14C, as the pump 320 is progressively actuated, the plunger 314 slides forwardly within the delivery device (or downwardly in FIGS. 14A-14C) due to the suction forces exerted thereon as the fluid is dispensed. One of the advantages of this embodiment is that substantially all surfaces in contact with the fluid contained in the storage chamber 316 and compression zone 339 may be formed of relatively rigid materials, such as the material described above and sold under the trademark TOPAZ. Note that although the piston tip 334 is shown as a resilient material, the surfaces of the piston tip that contact the fluid to be dispensed equally may be made of a rigid, less sorptive material, in the manner shown, for example, in FIG. 7. This type of configuration is particularly advantageous for purposes of making a "low sorption" device, or a device having desirable sorption characteristics. For example, in the above-mentioned example for storing and dispensing latanoprost formulations, this embodiment may be particularly advantageous from the perspective of sorption.

Figure 15:
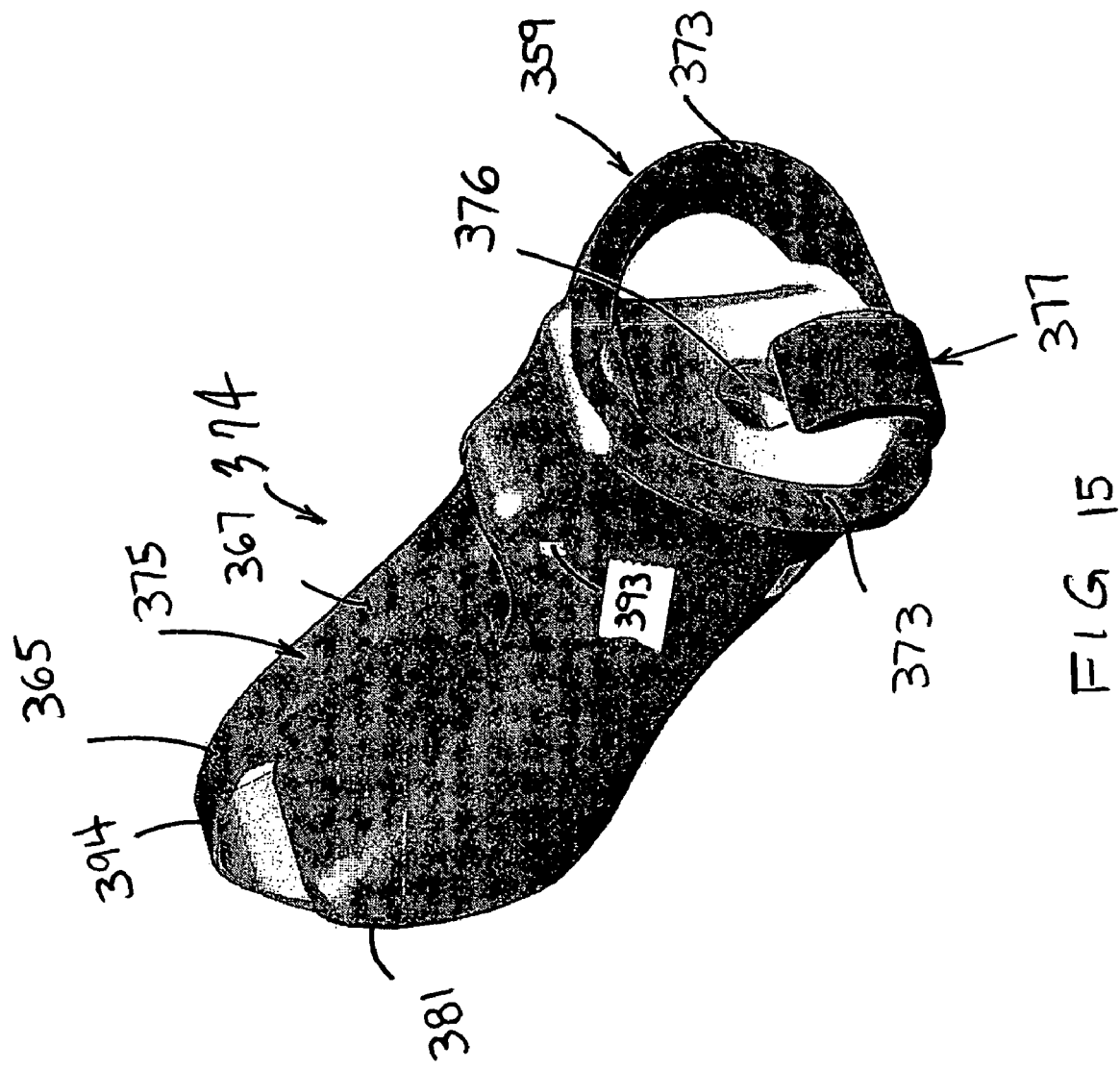
FIG. 15 is an upper perspective view of another embodiment of a housing for holding the exemplary embodiments of the delivery device and including an eye-cup, a trigger for actuating the pump, and an eyelid depressor for engaging facial tissue adjacent to the conjunctiva cul-de-sac of an eye to substantially simultaneously expose the cul-de-sac and deliver thereto a metered dosage of medicament or other substance from the delivery device.
Figure 16:
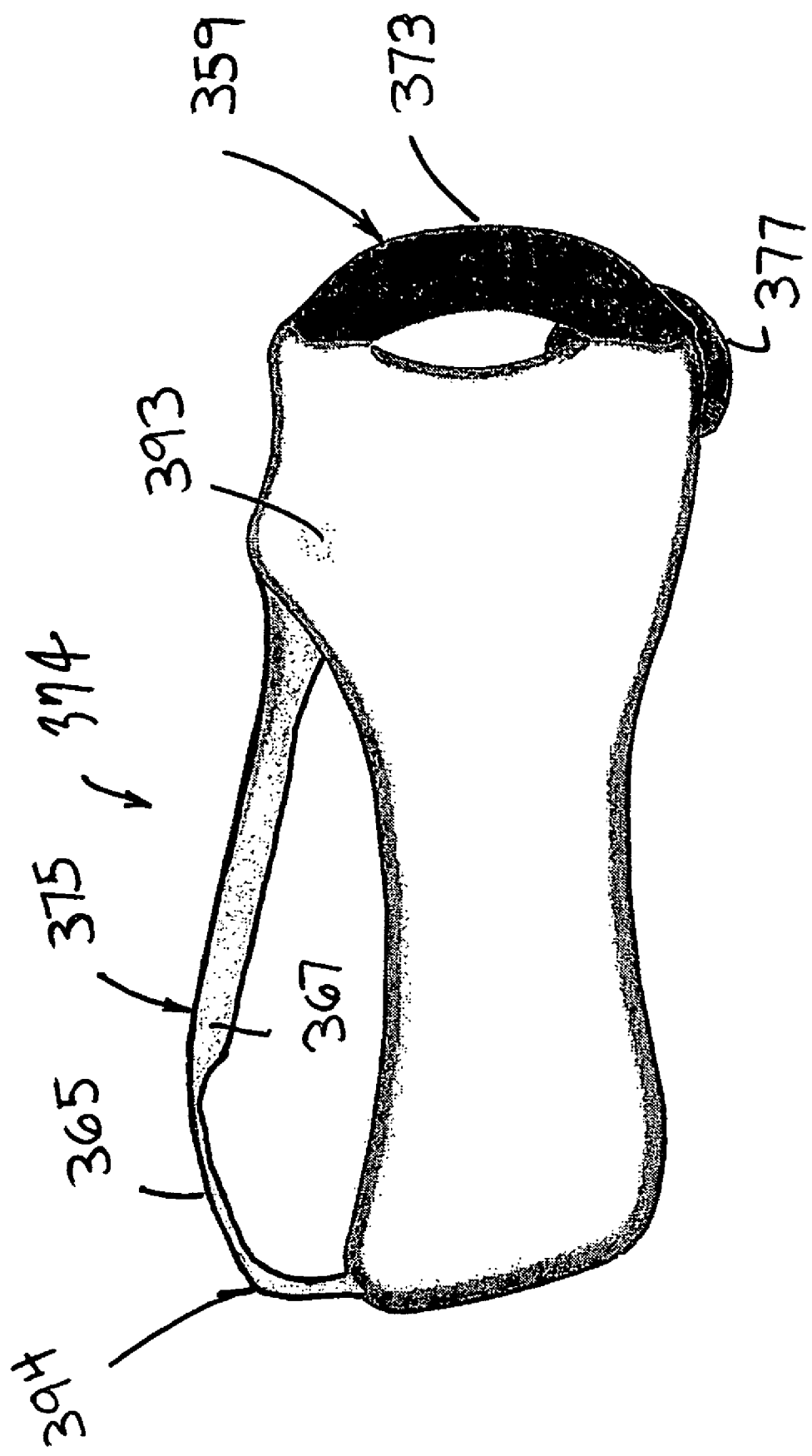
FIG. 16 is a side elevational view of the housing of FIG. 15.

In FIGS. 15 and 16, another housing that is usable with any of the disclosed delivery devices is indicated generally by the reference numeral 374. The housing 374 is similar to the housing 174 described above in connection with FIGS. 7-10, and therefore like reference numerals preceded by the numeral "3" instead of the numerals "1" or "2", are used to indicate like elements. A primary difference of the housing 374 in comparison to the housing 174 is that the end 394 of the trigger 375 is formed integral with the end wall 381 of the housing, and defines a living hinge 365 extending between the rear end 394 and relatively thicker and rigid body 367 of the trigger. The trigger 375 is actuated by depressing the body 367 inwardly toward the housing 374. This, in turn, causes the living hinge 365 to flex inwardly and thereby allow the inward movement of the trigger. One advantage of this embodiment of the invention is that the trigger 375 can be formed integral with the body of the housing, and thereby further reduce costs and/or the overall size of the housing.

Referring to FIGS. 17-20, another delivery device embodying the invention is indicated generally by the reference numeral 410. The delivery device 410 is similar to the delivery devices 110, 210, and 310 described above, and therefore like reference numerals preceded by the numeral "4" instead of the numerals "1", "2", or "3" are used to indicate like elements. Delivery device 410 is similar to delivery device 310 in that there is no flexible inner bladder. Rather, the delivery device 410 includes a slidable stopper 414 that extends between the rigid body 412 and the inner fill tube 450. The slidable stopper and the flexible bladder both function in the same manner in that both devices define a variable volume storage chamber 416 and help to push the fluid out of the body 412. It is noted that spaces 413 are used for the molding process only and are closed off and not functional on the nozzle. It is also noted that valve cover 424 is shown in two pieces 424a and 424b that are molded together.

Valve cover 424 is assembled onto the delivery device by sliding the valve cover 424 over valve seat 422. The body 412 includes an annular protuberance 401 and peripheral groove 403 that allows valve cover 424 to be secured into place at the body 412. It is also noted that at the width of the tip 405 of the valve cover 424 and the valve seat 422, the tip 405 is substantially smaller than a depth 407 of a recess 409 of the valve cover 424 and the valve seat 422. This allows the fluid that is exiting the interface 426 to move off of the tip 405 rather than sliding into the recess 409.

The body 412 also includes a grip portion 431 that is located adjacent to the annular flange 496. First and second drive arms 195 (see FIG. 8) are engageable with the annular flange 496 and grip portion 431. The body 412 also includes two nubs 427 and indents 429 that are located within the storage chamber 416. The nubs 427 and indents 429 mate with the shape of the slidable stopper 414 so as to have a substantially zero ullage or volume of fluid left in the storage chamber 416 when the storage chamber 416 has been emptied.

Figure 17:
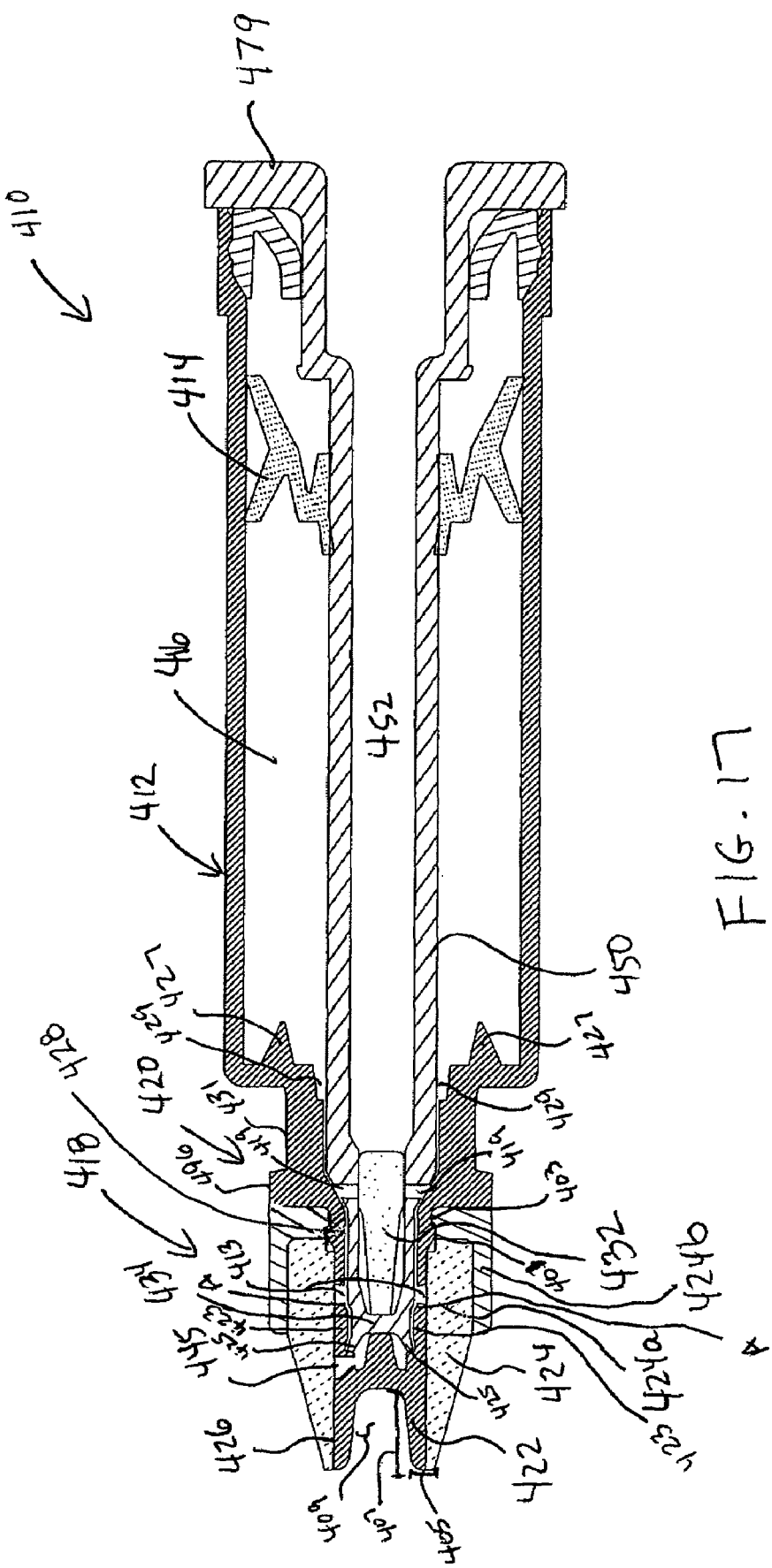
FIG. 17 is a cross-sectional view of another embodiment of a delivery device.
Figure 18:
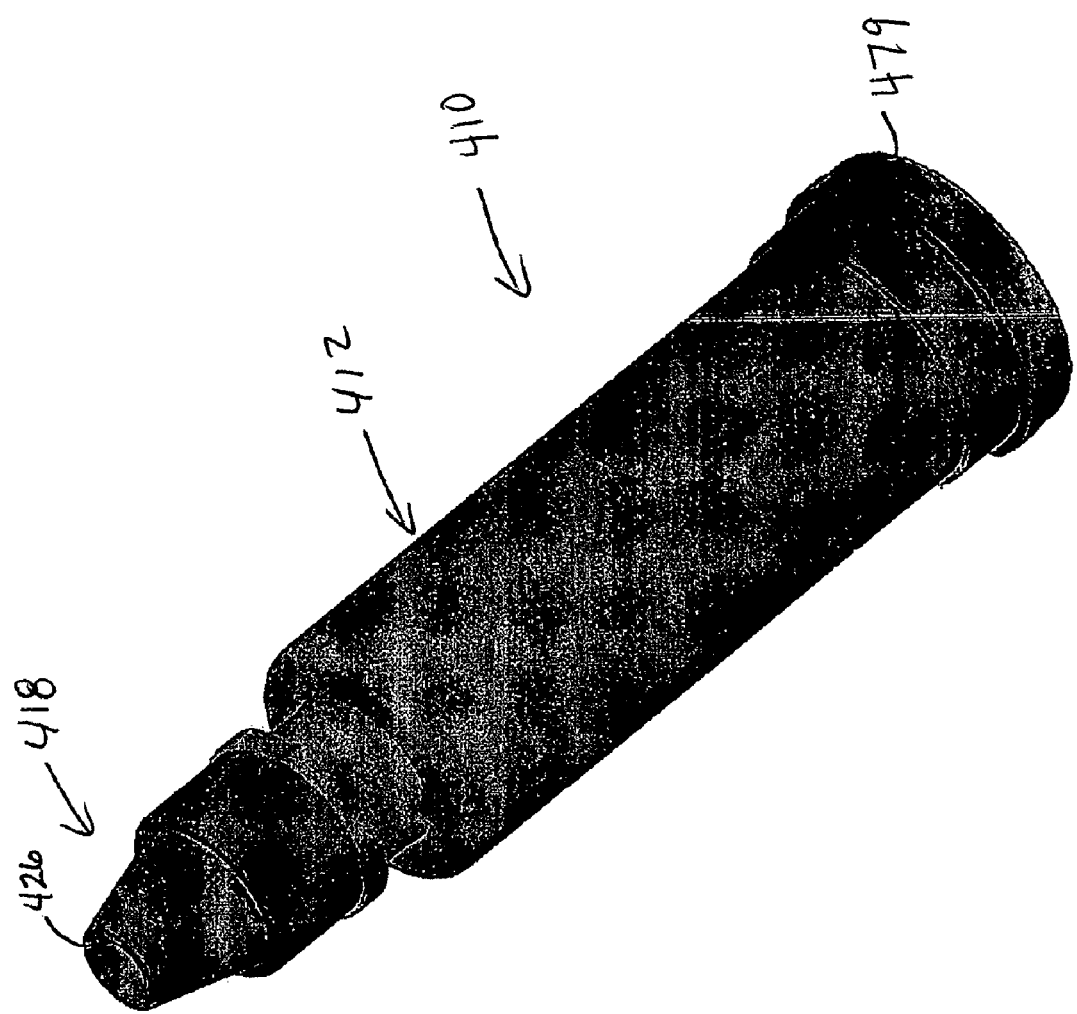
FIG. 18 is a perspective view of the delivery device of FIG. 17.

Valve seat 422 includes an interior shape 423 that mates with an outer edge 425 of the piston tip 434 so as to seal the dispenser 410 when the dispenser is in the closed position, which is illustrated in FIG. 17. When the body 412 slides relative to filling tube 450 and interior shape 423 of valve seat 422, piston tip 434 slides along the interior shape 423 until outer edge 425 reaches point A, which is shaped so as to allow fluid from storage chamber to flow through to outlet aperture 445 and interface 426.

The piston 432 is made of a flexible material that allows the piston 432 to be compressed. Thus, storage chamber 416 is filled with fluid by having a filling device (not shown) enter fluid conduit 452 and press down on piston 432, which compresses the piston 432 until filling apertures 419 are exposed and allows fluid to flow into storage chamber 416. It is noted that because the piston tip 434 remains in the closed (sealed) position during the filling process that fluid can only enter the storage chamber 416 and will not flow out through interface 426 when the storage chamber 416 is being filled.

Figure 19:
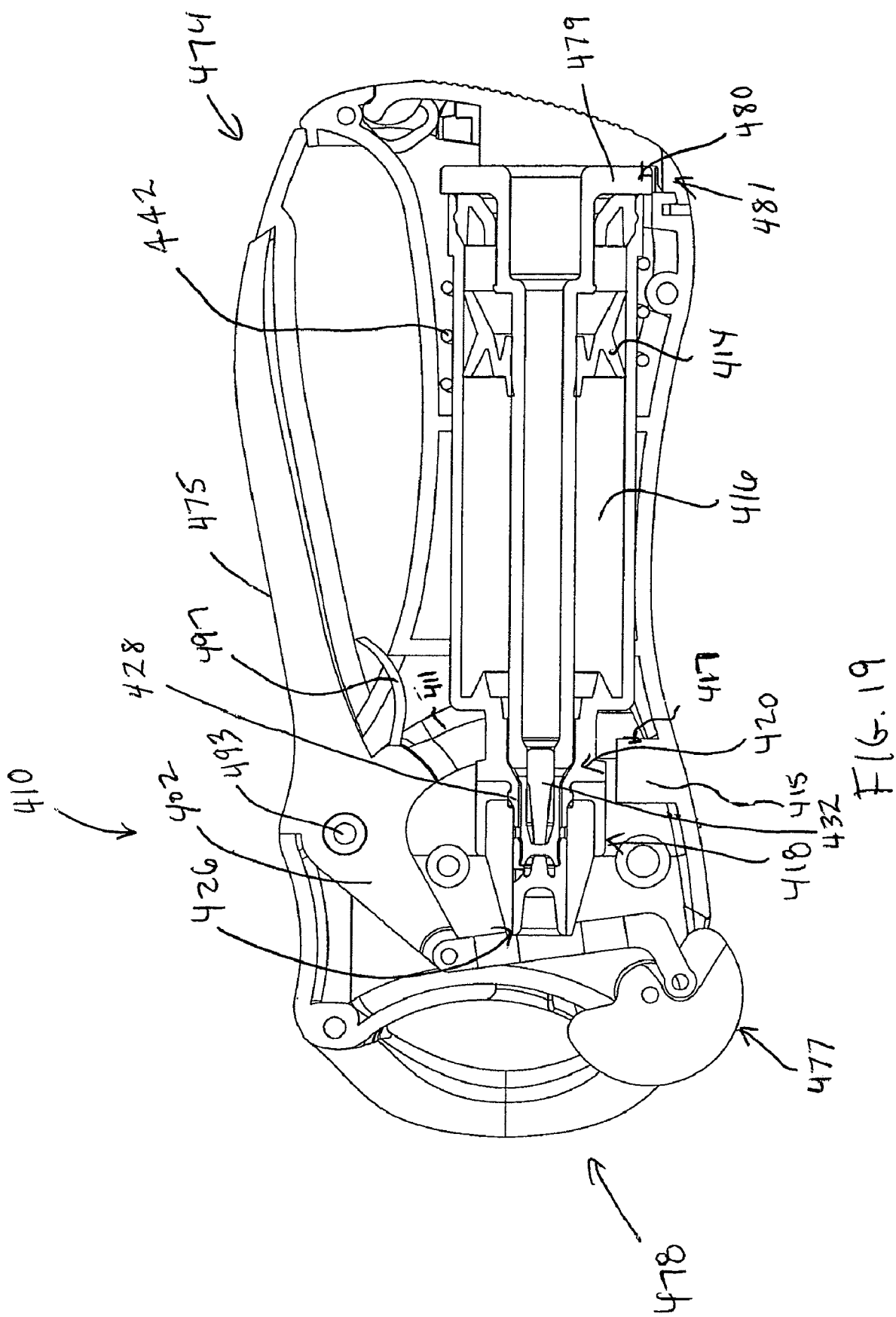
FIG. 19 is a cross-sectional view of the delivery device of FIG. 17 in another embodiment of a housing.

FIGS. 19 and 20 show the delivery device 410 as being mounted in a housing 474. It is understood that all of the other embodiments may also be mounted in the housing 474 in a similar manner. The delivery device 410 is mounted within the housing 474 including an actuator 475 for actuating the pump 420 of the delivery device; a dispensing aperture 478 aligned with the outlet interface 426 of the nozzle 418 for receiving therethrough a metered dosage of medicament, fluid or other substance from the storage chamber 416; and an eye-lid depressor 477 pivotally mounted on the housing adjacent to the dispensing aperture 478 for engaging the facial tissue adjacent to the conjunctiva cul-de-sac and substantially simultaneously exposing the cul-de-sac and dispensing the metered dosage therein.

The flange 479 of the delivery device 410 is fixedly secured at a portion 480 to a base wall 481 of the housing 474. Thus, this embodiment is similar to the embodiment shown in FIGS. 7 and 8 in that the pump 420 is actuated by moving the vial body 412, and the slide 428 formed integral with the vial body, relative to the piston 432, and the piston 432 is formed integral with the fill tube 450 and flange 479. As body 412 slides relative to piston 432 and piston tip 434, body 412 moves so that piston tip 434 is beyond slide 428 and the fluid can fill the dosage chamber (not shown). It is understood that because body 412 slides relative to piston 432 and fill tube 450, a spring 442 is utilized to bias the delivery device 410 back to the rest position (which is shown in FIGS. 17 and 19). Spring 442 has the same function as spring 42 in FIG. 1, but is located in a different place on delivery device 410.

Housing 474 also includes a preloaded flexible member 497 that returns drive member 402 when pressed. The housing 474 includes an engagement block 415 formed at the base of the housing and defining opposing lateral surfaces 417 (only one shown) that engage the drive arms 195 (see FIG. 8) and force the drive arms laterally outwardly with further movement thereof toward the front end of the housing.

As may be recognized by those of ordinary skill in the pertinent art based on the teachings herein, numerous changes and modifications may be made to the above-described and other embodiments of the present invention without departing from the spirit of the invention as defined in the claims. For example, the components of the delivery devices may be made of any of numerous different materials that are currently or later become known for performing the functions of such components. Similarly, the components of the delivery devices may take any of numerous different shapes and/or configurations. Also, the delivery devices may be used to dispense any of numerous different types of fluids or other substances for any of numerous different applications, including, for example, ophthalmic, nasal, dermatological, or other pharmaceutical or OTC applications. Further, the sterile filling machine used to fill the delivery devices may take any of numerous different configurations that are currently, or later become known for filling the delivery devices in accordance with the teachings of the present invention. Such sterile filling machines may vary significantly from the filling machine disclosed herein. For example, the filling machines may have any of numerous different mechanisms for sterilizing, feeding, evacuating and/or filling the delivery devices. Further, the filling valve need not be formed through the bladder, but may extend through the vial or otherwise may be coupled in fluid communication with the storage chamber to evacuate and/or fill the storage chamber. Alternatively, the delivery device may include one valve for evacuating the interior of the delivery device and another valve for filling the storage chamber of the delivery device. Still further, the pump and/or dispensing valve each may take a configuration that is different than that disclosed herein. Accordingly, this detailed description of currently preferred embodiments is to be taken in an illustrative, as opposed to a limiting sense.

The invention claimed is:

1. An ophthalmic delivery device comprising:
    a body defining a fluid reservoir;
    a dosage chamber for holding a dosage of fluid;
    a nozzle including a valve seat and a valve cover, wherein the valve cover extends about the valve seat and forms an interface therebetween, and the interface defines an inlet in fluid communication with the dosage chamber and an outlet for dispensing fluid therethrough; and
    a pump in fluid communication with the reservoir and dosage chamber;
    wherein at least part of the valve cover is movable between (i) a closed position with the valve cover engaging the valve seat to close the interface and form a fluid-tight seal therebetween, and (ii) at least one open position with at least part of the valve cover spaced away from the valve seat in response to fluid flowing from the dosage chamber and into the inlet of the interface at a pressure greater than a valve opening pressure to allow the passage of pressurized fluid between the valve cover and valve seat;
    wherein the dosage chamber defines a first cross-sectional area and the valve seat defines a second cross-sectional area at the inlet to the interface with the valve cover greater than the first cross-sectional area to dispense each dosage of fluid through the interface at a velocity of less than approximately 10 meters per second.

2. The ophthalmic delivery device as defined in claim 1, wherein the pump comprises a slide defining a passageway and a piston slidably received within the passageway, wherein the slide defines within the passageway a compression zone forming the dosage chamber, a first portion formed between the compression zone and the reservoir, and a second portion located on an opposite side of the compression zone relative to the first portion, wherein the first portion is defined by a first cross-section and the compression zone is defined by a second cross-section that is less than the first cross-section, and at least one of the piston and slide is movable relative to the other between (i) a first position with a tip of the piston received within the first portion of the slide, and the compression zone coupled in fluid communication with the reservoir for receiving fluid therefrom, and (ii) a second position with the tip of the piston received within the second portion of the slide.

3. The ophthalmic delivery device as defined in claim 2, further comprising a spring drivingly connected to at least one of the body, the piston, and the slide, wherein the spring drives at least one of the body, the piston, and the slide from the first position to the second position to pressurize fluid in the compression zone and, in turn, dispense a dosage of fluid through the nozzle.

4. The ophthalmic delivery device as defined in claim 2, wherein the tip of the piston is softer than the compression zone of the slide, and the tip and the compression zone form an interference fit to thereby form a fluid-tight seal therebetween.

5. The ophthalmic delivery device as defined in claim 2, wherein the tip defines an annular base portion that forms an interference fit with the first portion of the slide and a fluid-tight seal therebetween.

6. The ophthalmic delivery device as defined in claim 2, wherein at least one of the piston and the slide is movable relative to the other from (i) a rest position with the piston tip located in the second portion of the slide; (ii) to a first actuated position with the piston tip located in the first portion of the slide and the compression zone coupled in fluid communication with the reservoir for receiving fluid therefrom; (iii) to a second actuated position with the piston tip located in the compression zone, a fluid tight seal formed between the piston tip and compression zone to pressurize the fluid in the compression zone to a pressure greater than the valve opening pressure and, in turn, cause the pressurized fluid to open the valve and dispense through the valve; and (iv) to the rest position with the piston tip located in the second portion of the slide and the outlet aperture coupled in fluid communication with the reservoir to reduce the pressure between the outlet aperture and the compression zone and allow closure of the valve.

7. The ophthalmic delivery device as defined in claim 6, wherein the nozzle defines a stop surface that contacts the piston tip in the rest position, and the surfaces of the piston tip and stop surface cooperate to define substantially zero volume within the second portion of the slide when the piston tip is in the rest position.

8. The ophthalmic delivery device as defined in claim 7, wherein the stop surface defines a first morphology, and the piston tip defines a second morphology substantially conforming to the first morphology.

9. The ophthalmic delivery device as defined in claim 1, further comprising a flexible bladder received within the body, and wherein the fluid reservoir defines a variable-volume storage chamber between the bladder and body.

10. The ophthalmic delivery device as defined in claim 1, further comprising a filling valve in fluid communication with the reservoir, wherein the filling valve includes a flexible filling valve member, and a filling valve seat engagable with the flexible filling valve member, wherein the flexible filling valve member is movable into a closed position in engagement with the filling valve seat to form a fluid-tight seal therebetween, and an open position spaced away from the filling valve seat and forming a filling valve opening for the passage of fluid therebetween.

11. The ophthalmic delivery device as defined in claim 1, further comprising a filling valve in fluid communication with the reservoir, wherein the filling valve includes a flexible filling valve member movable between closed and open positions, and a spring coupled to the flexible valve member and biasing the flexible filling valve member toward the closed position.

12. The ophthalmic delivery device as defined in claim 1, wherein the valve cover forms an interference fit with the valve seat to form the fluid-tight seal therebetween, and the valve cover defines a progressively decreasing wall thickness in a direction from an interior toward an exterior of the delivery device.

13. The ophthalmic delivery device as defined in claim 1, further comprising manually-engageable actuator drivingly connected to the pump for moving the pump from a rest position to an actuated position.

14. The ophthalmic delivery device as defined in claim 13, wherein the actuator includes a trigger and a lever arm drivingly connected between the trigger and the pump for moving the pump from the rest position to the actuated position in response to movement of the trigger.

15. The ophthalmic delivery device as defined in claim 1, further comprising a housing surrounding the body, the pump, and the nozzle, wherein the housing includes an opening and the nozzle is positioned to dispense the dosage of fluid through the opening.

16. The ophthalmic delivery device as defined in claim 15, wherein the housing includes an eyelid depressor for engaging facial tissue adjacent to an eye and lowering the eyelid to expose an ocular cul-de-sac upon delivering a dosage thereto, and wherein the outlet of the nozzle interface is aligned with the eyelid depressor for delivering a dosage to the exposed ocular cul-de-sac.

17. The ophthalmic delivery device as defined in claim 15, wherein the housing includes a support surface coupled to the body for engaging facial tissue adjacent to an eye and setting an approximate delivery distance between an anterior end of the nozzle and the eye.

18. The ophthalmic delivery device as defined in claim 15, wherein the nozzle is positioned within the housing so that a delivery distance of the dosage of fluid is within the range of approximately 3 centimeters through approximately 10 centimeters.

19. The ophthalmic delivery device as defined in claim 1, wherein at least one of an interference between the valve seat and the valve cover and an axial length of the interface is dimensioned to dispense the dosage of fluid through the interface at a velocity of equal to or less than about 10 meters per second.

20. The ophthalmic delivery device as defined in claim 1, wherein at least one of an interference between the valve seat and the valve cover and an axial length of the interface is dimensioned to release the dosage of fluid in a plurality of micro-droplets.

21. The ophthalmic delivery device as defined in claim 20, wherein the energy of each micro-droplet upon exiting the delivery device is less than approximately 5 micro-joules.

22. The ophthalmic delivery device as defined in claim 2, wherein a linear surface area of the interface is greater than a linear surface area of the compression zone.

23. An ophthalmic delivery device comprising:
first means for defining a variable-volume chamber and for storing an ophthalmic substance to be delivered to an eye;
second means for metering a dose of substance from the variable-volume chamber at a volume within the range of about 15 to about 25 micro liters and for pressurizing the metered dose above a valve opening pressure;
third means in fluid communication with the second means for (i) forming a closed position defining a fluid-tight seal for preventing the passage of substance therethrough, and (ii) at least one open position for allowing a the metered dose of substance pressurized by the second means at a pressure greater than the valve opening pressure to flow therethrough; and
fourth means for delivering the metered dosage in a plurality of micro droplets at a velocity exiting the third means of less than approximately 10 meters per second.

24. The ophthalmic delivery device as defined in claim 23, further comprising:
fifth means for actuating the second means; and
sixth means for engaging facial tissue adjacent to an eye for exposing at least a portion of a conjunctiva cul-de-sac for delivering a metered dose of substance thereon.

25. The ophthalmic delivery device as defined in claim 24, wherein the sixth means engages the facial tissue substantially simultaneously with the fifth means actuating the second means.

26. The ophthalmic delivery device as defined in claim 23, wherein the fourth means delivers the pumped dosage at a velocity exiting the third means of less than approximately 6 meters per second.

27. The ophthalmic delivery device as defined in claim 23, wherein the first means is a body of the device defining therein the variable-volume chamber; the second means is a pump; the third means is a one-way valve; and the fourth means is (i) at least one of an interference of a valve cover and a valve seat of the one-way valve, and an axial length of an interface between the valve cover and the valve seat, being dimensioned to dispense the dosage in a plurality of micro droplets at a velocity of less than approximately 10 meters per second, and (ii) a dosage chamber of the pump defining a first cross-sectional area and the valve seat defining a second cross-sectional area at an inlet to the interface with the valve cover greater than the first cross-sectional area.

28. A method for delivering a substance to an eye, comprising:
(i) storing multiple doses of the substance hermetically sealed in a variable-volume chamber connectible in fluid communication with a one-way valve defining a normally closed valve opening that opens in response to the substance at an inlet to the valve opening exceeding a valve opening pressure;
(ii) metering a dose of substance from the variable-volume storage chamber at a volume within the range of about 15 micro liters to about 25 micro liters and pressurizing the metered dose above the valve opening pressure;
(iii) introducing the pressurized metered dose through the one way valve; and
(iv) delivering the metered dose from the one way valve in a plurality of micro droplets at a velocity of less than approximately 10 meters per second and into the eye.

29. A method as defined in claim 28, wherein step (iv) includes delivering the metered dose at a velocity of less than approximately 6 meters per second.

30. A method as defined in claim 28, further comprising engaging with a tissue-engaging member facial tissue adjacent to the eye to at least partially expose the conjunctiva cul-de-sac, and wherein step (iv) includes delivering the metered dose to the conjunctiva cul-de-sac.

31. The ophthalmic delivery device as defined in claim 1, wherein the dosage chamber is defined by a first radius, and the valve seat is defined by a second radius at the inlet to the interface with the valve cover that is greater than the first radius.

32. The ophthalmic delivery device as defined in claim 31, wherein the dosage chamber defines a first diameter, and the valve seat defines a second diameter at the inlet to the interface with the valve cover that is greater than the first diameter.

33. The ophthalmic delivery device as defined in claim 1, wherein the dosage chamber is defined by a wall spaced a first radial distance about an elongated axis of the device, and the valve seat is spaced a second radial distance about the elongated axis of the device that is greater than the first radial distance.

34. The ophthalmic delivery device as defined in claim 1, further including a flow aperture in fluid communication between the dosage chamber and the inlet to the interface, wherein an inlet end of the flow aperture defines a first cross-sectional area and an outlet end of the flow aperture defines a second cross-sectional area that is greater than the first cross-sectional area.

35. The ophthalmic delivery device as defined in claim 34, wherein the outlet aperture is oriented at an oblique angle relative to an elongated axis of the device.

36. The ophthalmic delivery device as defined in claim 34, wherein the outlet aperture extends angularly throughout an arc about an elongated axis of the device.

37. The ophthalmic delivery device as defined in claim 36, wherein the device is mounted within a housing defining a facial engaging surface for engaging facial tissue adjacent to an eye, and the outlet aperture is angularly positioned within the housing such that is it aligned with an ocular cul-de-sac of an eye with the facial engaging surface engaging facial tissue adjacent to the eye.

38. The method as defined in claim 28, wherein step (iv) includes delivering the metered dose at an energy upon impacting the eye that is equal to or less than approximately 40 micro-joules.

39. The method as defined in claim 28, further comprising repeating steps (ii) through (iv) a plurality of times at spaced time intervals relative to each other.

40. The method as defined in claim 28, wherein step (iv) includes delivering the metered dose in a plume of micro droplets that extend through an approximately semi-circular arc that substantially conforms to the angular extent of a conjunctiva cul-de-sac.

* * * * *